(12) United States Patent
Donnelly et al.

(10) Patent No.: US 8,609,109 B2
(45) Date of Patent: Dec. 17, 2013

(54) HIV VACCINE FORMULATIONS

(75) Inventors: John Donnelly, Moraga, CA (US); Susan W. Barnett, San Francisco, CA (US); Derek O'Hagan, Winchester, MA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 13/334,739

(22) Filed: Dec. 22, 2011

(65) Prior Publication Data

US 2012/0207783 A1    Aug. 16, 2012

Related U.S. Application Data

(60) Division of application No. 12/364,294, filed on Feb. 2, 2009, now abandoned, which is a continuation of application No. 10/530,543, filed as application No. PCT/US03/31935 on Oct. 7, 2003, now abandoned.

(60) Provisional application No. 60/416,573, filed on Oct. 7, 2002.

(51) Int. Cl.
*A61K 39/21*     (2006.01)
*A61P 37/04*     (2006.01)

(52) U.S. Cl.
USPC .................. 424/208.1; 530/300; 536/23.1

(58) Field of Classification Search
None
See application file for complete search history.

(56) References Cited

U.S. PATENT DOCUMENTS

| | | | |
|---|---|---|---|
| 5,603,960 A | 2/1997 | O'Hagan et al. | |
| 5,643,605 A | 7/1997 | Cleland et al. | |
| 6,086,901 A | 7/2000 | O'Hagan et al. | |
| 6,099,847 A | 8/2000 | Tobin et al. | |
| 6,171,596 B1 * | 1/2001 | Earl et al. | 424/208.1 |
| 6,306,405 B1 | 10/2001 | O'Hagan et al. | |
| 6,458,370 B1 | 10/2002 | O'Hagan et al. | |
| 6,514,524 B1 | 2/2003 | Saslawski et al. | |
| 6,602,705 B1 | 8/2003 | Barnett et al. | |
| 6,753,015 B2 | 6/2004 | Fang et al. | |
| 6,855,492 B2 | 2/2005 | O'Hagan et al. | |
| 6,884,435 B1 | 4/2005 | O'Hagan et al. | |
| 7,211,659 B2 | 5/2007 | zur Megede | |
| 2003/0049298 A1 | 3/2003 | O'Hagan et al. | |
| 2003/0050263 A1 | 3/2003 | Krieg et al. | |
| 2003/0138453 A1 | 7/2003 | O'Hagan et al. | |
| 2003/0170614 A1 | 9/2003 | Megede et al. | |
| 2003/0191076 A1 | 10/2003 | Wesselingh et al. | |
| 2003/0194800 A1 | 10/2003 | Megede et al. | |
| 2003/0198621 A1 | 10/2003 | Megede et al. | |
| 2003/0199071 A1 * | 10/2003 | Langermann et al. | 435/200 |
| 2003/0223964 A1 | 12/2003 | Barnett et al. | |
| 2004/0022814 A1 | 2/2004 | O'Hagan et al. | |
| 2004/0156913 A1 | 8/2004 | Fang et al. | |
| 2005/0136073 A1 | 6/2005 | O'Hagan et al. | |
| 2005/0191319 A1 | 9/2005 | O'Hagan et al. | |
| 2005/0191358 A1 | 9/2005 | O'Hagan et al. | |
| 2005/0214256 A1 | 9/2005 | zur Megede et al. | |

FOREIGN PATENT DOCUMENTS

| | | |
|---|---|---|
| WO | WO-98/33487 | 8/1998 |
| WO | WO-99/30737 | 6/1999 |
| WO | WO-00/06123 | 2/2000 |
| WO | WO-01/52886 | 2/2000 |
| WO | WO-02/26209 | 7/2001 |
| WO | WO-02/26212 | 4/2002 |
| WO | WO-2004/065578 | 8/2004 |

OTHER PUBLICATIONS

O'Hagan et al. (Journal of Virology, Oct. 1, 2001, vol. 75, p. 9037-9043).*
Srivastava et al., (Journal of Virology, 2002, vol. 76, p. 2835-2847).*
Barnett SW. et al., (Jun. 2001) "The ability of an oligomeric human immunodeficiency virus type 1 (HIV-1) envelope antigen to elicit neutralizing antibodies against primary HIV-1 isolates is improved following partial deletion of the second hypervariable region ," J Virol. Jun. 2001;75(12):5526-40.
Cherpelis et al. (Feb. 2001) "DNA vaccination with the Human Immunodeficiency Virus Type 1 SF162-deltaV2 envelope elicits immune responses that offer partial protection from Simian/Human Immunodeficiency Virus infection to CD8+ T-Cell-depleted Rhesus macaques," J Virol 75(3):1547-1551.
Jeffrey H. et al., (1993) "The preparation and characterization of poly(lactide-co-glycolide) microparticles. 11. The Entrapment of a model protein using a (water-in-oil)-in-water emulsion solvent evaporation technique," Pharm. Res. 10(3):362-368.
Letvin NL., (Dec. 2006) "Progress and obstacles in the development of an AIDS vaccine." Nat Rev Immunol. 6(12):930-9.
Machuca A. et al., (1999) "Human immunodeficiency virus type 2 infection in Spain. The HIV-2 Spanish Study Group," Intervirology 42(1):37-42.
Otten et al. (May 2003) "Induction of broad and potent anti-human immunodeficiency virus immune responses in rhesus macaques by priming with a DNA vaccine and boosting with protein-adsorbed polylactide coglycolide microparticles," J Virol 77(10):6087-6092.
Srivastava IK. et al., (Oct. 2003) "Purification, characterization, and immunogenicity of a soluble trimeric envelope protein containing a partial deletion of the V2 loop derived from SF162, an R5-tropic human immunodeficiency virus type 1 isolate," J Virol. 77(20):11244-59.
Ugen et al. (Nov. 1998) "DNA vaccination with HIV-a expressing constructs elicits immune responses in humans," Vaccine 16(19):1818-1821.

* cited by examiner

*Primary Examiner* — Agnieszka Boesen
(74) *Attorney, Agent, or Firm* — Helen Lee; Regina Bautista; Otis Littlefield

(57) ABSTRACT

Provided herein are HIV vaccines comprising HIV polypeptide-encoding DNA adsorbed to PLG and/or HIV proteins. Also provided are methods of using these vaccines to generate immune responses in a subject.

16 Claims, 6 Drawing Sheets

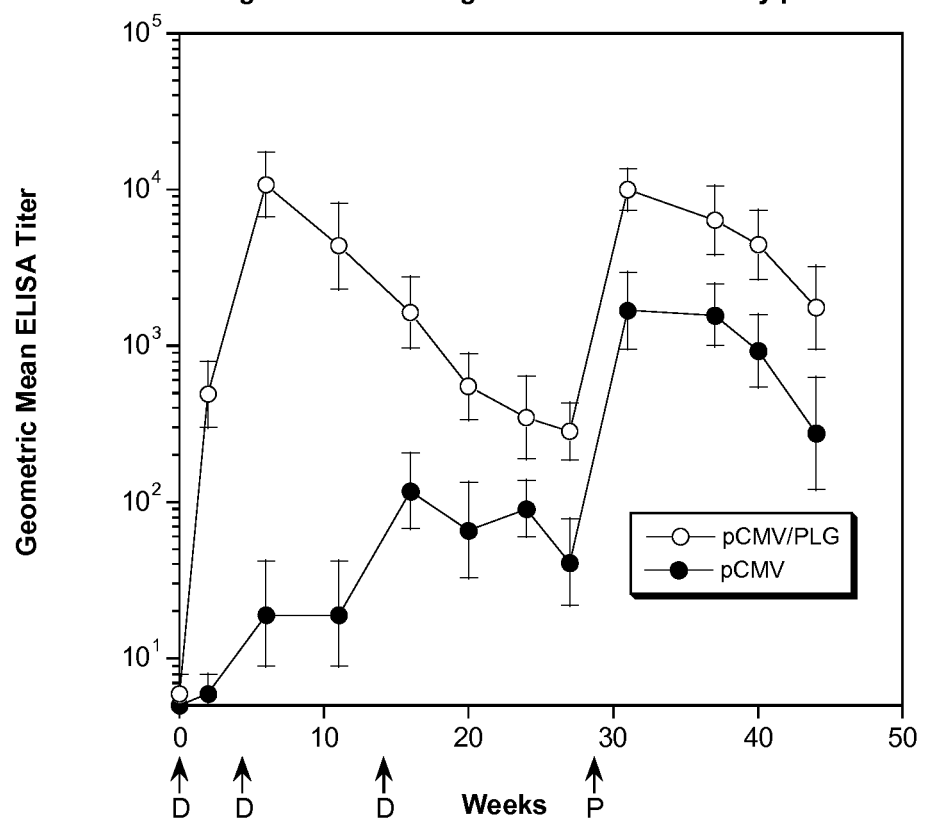

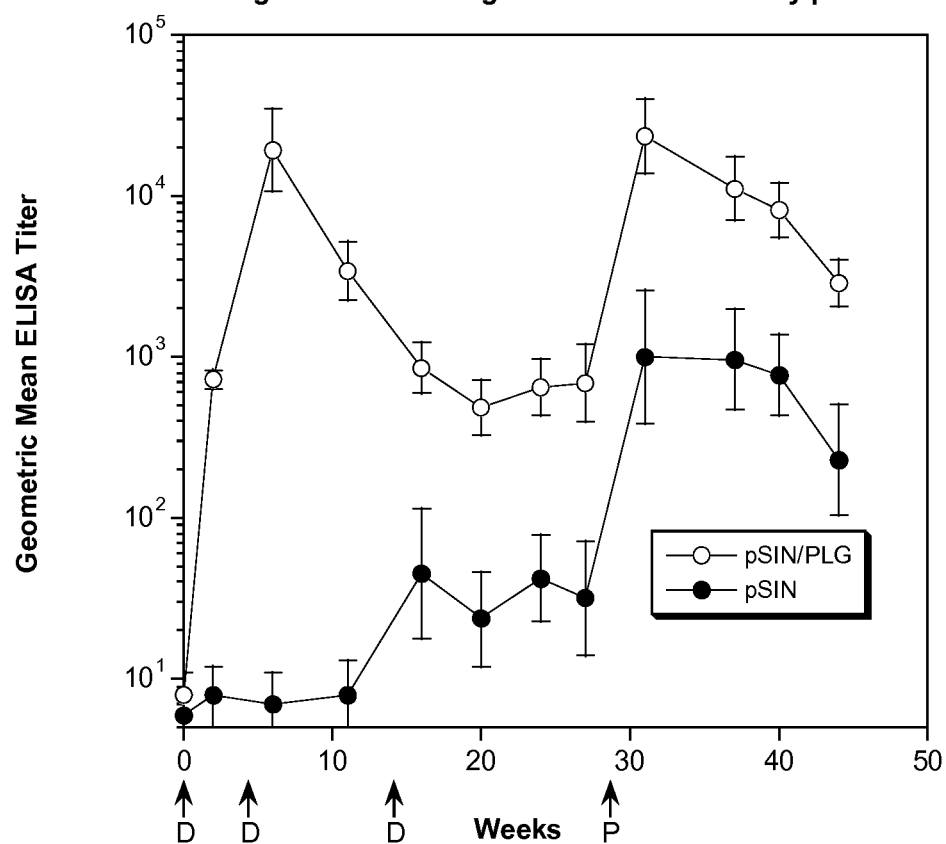

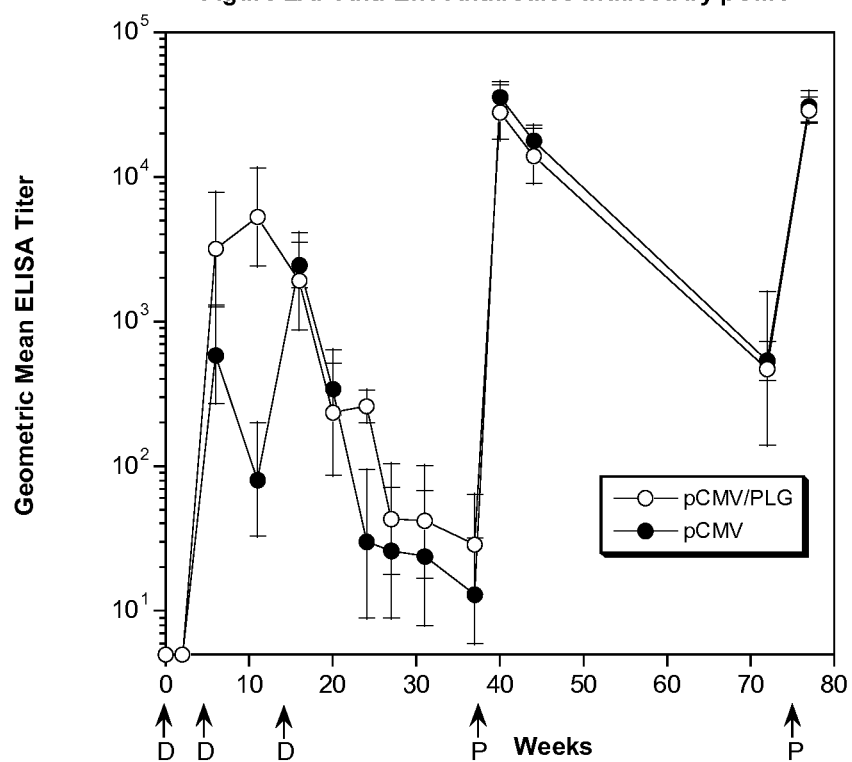

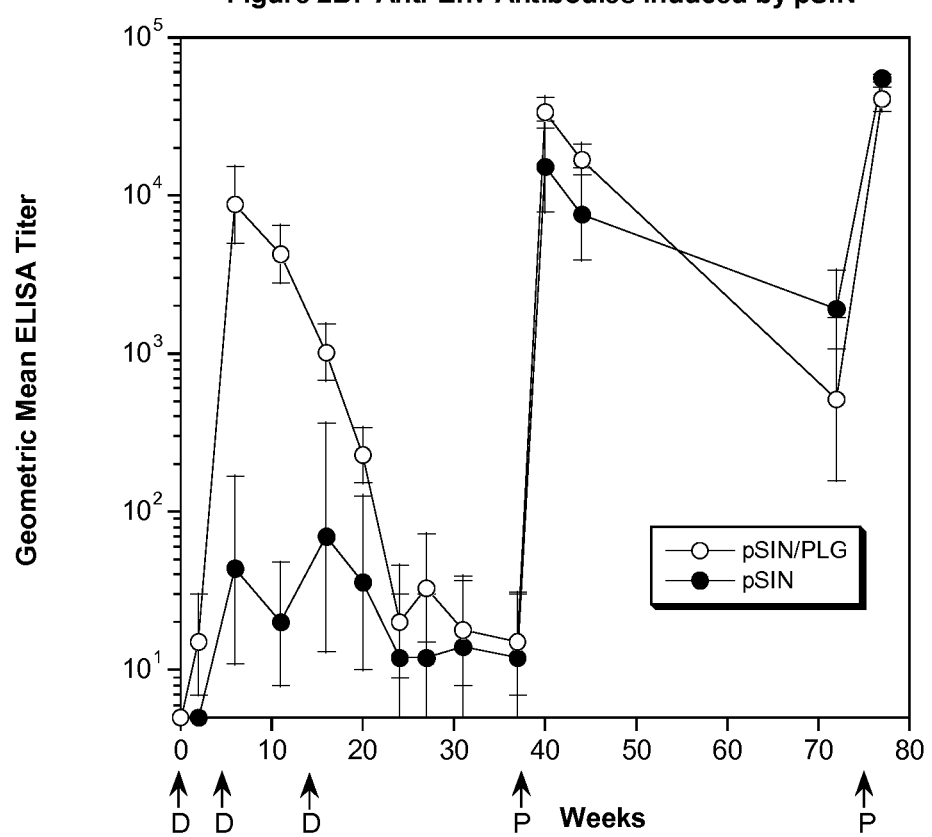

HIV VACCINE FORMULATIONS

CROSS REFERENCE TO RELATED APPLICATIONS

This application is a divisional of Ser. No. 12/364,294, filed Feb. 2, 2009, which is a continuation of Ser. No. 10/530,543, which is the U.S. National Phase of International Application No. PCT/US2003/031935, filed Oct. 7, 2003, which claims the benefit of U.S. Provisional Application No. 60/416,573, filed Oct. 7, 2002. The above applications are incorporated in their entirety by reference.

GOVERNMENT SUPPORT

The invention was supported, in whole or in part, by NIH HIVDDT Grant No. N01-AI-05396 from the National Institutes of Health. The Government has certain rights in the invention.

TECHNICAL FIELD

The present invention relates generally to immunogenic HIV compositions, in particular to HIV vaccines and methods of formulating and administering these vaccines.

BACKGROUND

Acquired immune deficiency syndrome (AIDS) is recognized as one of the greatest health threats facing modern medicine. There is, as yet, no cure for this disease.

In 1983-1984, three groups independently identified the suspected etiological agent of AIDS. See, e.g., Barre-Sinoussi et al. (1983) Science 220:868-871; Montagnier et al., in Human T-Cell Leukemia Viruses (Gallo, Essex & Gross, eds., 1984); Vilmer et al. (1984) The Lancet 1:753; Popovic et al. (1984) Science 224:497-500; Levy et al. (1984) Science 225: 840-842. These isolates were variously called lymphadenopathy-associated virus (LAV), human T-cell lymphotropic virus type III (HTLV-III), or AIDS-associated retrovirus (ARV). All of these isolates are strains of the same virus, and were later collectively named Human Immunodeficiency Virus (HIV). With the isolation of a related AIDS-causing virus, the strains originally called HIV are now termed HIV-1 and the related virus is called HIV-2. See, e.g., Guyader et al. (1987) Nature 326:662-669; Brun-Vezinet et al. (1986) Science 233:343-346; Clavel et al. (1986) Nature 324:691-695.

Since the implementation of highly active antiretroviral therapy (HAART) in the United States in 1996, the number of persons diagnosed with acquired immunodeficiency syndrome (AIDS) and the number of deaths among persons with AIDS have declined substantially (Karon et al. (2001) Am J Public Health 91(7):1060-1068) as a result, the number of persons living with AIDS has increased. The Centers for Disease Control (CDC) estimates that as of Dec. 31, 2000, approximately 340,000 persons in the United States were living with AIDS. (MMWR, Centers for Disease Control and Prevention. HIV/AIDS Surveillance Report, 13(No. 1) 2001).

Clinical trials in the US have been conducted with a limited number of subjects and further HIV vaccine development will require the identification of a suitable population where the HIV seroincidence is sufficiently high to enable a distinction between protection in the immunized population with a placebo control. Seage III et al. (2001) Am. J. Epidemiol. 153 (7):619-627; Halpern et al. (2001) J Acquir Immune Defic Syndr 27(3):281-8.

The primary mode of transmission of HIV is through sex and by contact with infected body fluids including blood, semen, vaginal fluid, breast milk, and other body fluids containing blood. In industrialized countries, the majority of cases reported in which the person's risk is known are among men who have sex with men. Before blood screening for antibodies to HIV was instituted, transfusion-associated HIV was a concern in the US. (CDC. Update: HIV-2 infection among blood and plasma donors—United States, June 1992-June 1995. MMWR, 1995. 44: p. 603-606). Other modes of transmission include needle sharing by injection drug users, inadvertent contact with infected blood among hospital workers, and rare iatrogenic transmission through the re-use of contaminated medical equipment. Higher rates of sexually transmitted infections signal a rise in unsafe sex practices. Chen et al. (2001) Am J Public Health 92(9):1387-1388. Heterosexual transmission of HIV-1 continues to rise, particularly among women, the young, and the economically disadvantaged and, in fact, heterosexual transmission is the dominant mode of transmission in the developing world. These trends highlight the need for the development of a preventive and/or therapeutic vaccine. Catania et al. (2001) Am J Public Health 91(6):907-914.

Several targets for vaccine development have been examined, including the env and Gag gene products encoded by HIV. Gag gene products include, but are not limited to, Gag-polymerase (pol) and Gag-protease (prot). Env gene products include, but are not limited to, monomeric gp120 polypeptides, oligomeric gp140 polypeptides (o-gp140) and gp160 polypeptides.

Recently, use of HIV Env polypeptides in immunogenic compositions has been described. (see, U.S. Pat. No. 5,846, 546 to Hurwitz et al., issued Dec. 8, 1998, describing immunogenic compositions comprising a mixture of at least four different recombinant virus that each express a different HIV env variant; and U.S. Pat. No. 5,840,313 to Vahlne et al., issued Nov. 24, 1998, describing peptides which correspond to epitopes of the HIV-1 gp120 protein). In addition, U.S. Pat. No. 5,876,731 to Sia et al, issued Mar. 2, 1999 describes candidate vaccines against HIV comprising an amino acid sequence of a T-cell epitope of Gag linked directly to an amino acid sequence of a B-cell epitope of the V3 loop protein of an HIV-1 isolate containing the sequence GPGR. However, these groups did not identify an effective HIV vaccine.

U.S. Pat. No. 6,602,705 and International Patent Publications WO 00/39302; WO 02/04493; WO 00/39303; and WO 00/39304 describe polynucleotides encoding immunogenic HIV polypeptides from various subtypes.

Thus, there remains a need for immunogenic HIV compositions, specifically for HIV vaccine formulations.

SUMMARY

In one aspect, the invention includes an HIV DNA vaccine composition comprising a nucleic acid expression vector (e.g., plasmid, viral vector, etc.) comprising at least one HIV Gag- or Env-encoding sequence and PLG. Preferably, the nucleic acid expression vector is adsorbed to the PLG. In certain embodiments, the concentration of PLG is between about 5 and 100 fold greater than the concentration of the nucleic acid expression vector. For example, the concentration of nucleic acid can be between about 10 µg/mL and 5 mg/mL and the concentration of the PLG can be between about 100 µg/mL and 100 mg/mL and/or the nucleic acid expression vector concentration per dose can be between approximately 1 µg/dose and 5 mg/dose and the PLG concentration per dose can be between approximately 10 µg/dose and 100 mg/dose. Specific formulations are described herein, for example, in Table 1, Table 2, or column 2 of Table 9.

In another aspect, the invention includes an HIV vaccine composition comprising an HIV envelope protein, for example oligomeric gp140 (o-gp140); and a pharmaceutically acceptable excipient. In certain embodiments, the concentration of o-gp140 is between about 0.1 mg/mL and 10 mg/mL. Further, in certain embodiments, the concentration of o-gp140 per dose is approximately 100 μg/dose. Specific formulations of HIV protein vaccines are also described herein, for example in Table 3 and Table 11.

In another aspect, the invention comprises an HIV vaccine including one or more of the HIV DNA vaccines described herein (e.g., an HIV Gag DNA vaccine as described herein and an HIV Env DNA vaccine as described herein) and one or more of the HIV vaccines described herein (e.g., an HIV o-gp140 preparation).

Any of the HIV vaccine compositions described herein may further include one or more adjuvants, for example MF59 or CpG. A particular formulation for MF59 is set forth in Table 4.

In yet another aspect, the invention includes a method of generating an immune response in a subject, comprising (a) administering at least one HIV vaccine composition described herein to the subject, and (b) administering, at a time subsequent to the administering of step (a), at least one HIV vaccine composition described herein. In certain embodiments, the at least one HIV vaccine composition administered in step (a) comprises an HIV DNA vaccine (e.g., at least one HIV Gag vaccine and/or at least one HIV Env vaccine) as described herein and the HIV vaccine composition administered in step (b) comprises an HIV protein vaccine as described herein. Furthermore, step (a) may comprise multiple administrations of one or more HIV DNA vaccines as described herein (e.g., two or three administrations at one month intervals) and step (b) may comprise at least one administration of one or more HIV protein vaccines as described herein (e.g., two or three administrations at 1, 2, or 3 month intervals). Alternatively, step (b) may comprise concurrently administering at least one HIV DNA vaccine described herein (e.g., an HIV Gag vaccine and/or an HIV Env vaccine) and at least one and at least one HIV protein vaccine as described herein. The time between the administrations of step (a) and step (b) can vary, for example between 1 to 6 months or even longer. In any of the methods described herein, one or more administrations may be intramuscular and/or intradermal.

In a further aspect, the invention includes a method of making oligomeric HIV Env gp140 proteins, comprising the steps of introducing a nucleic acid encoding gp140 into a host cell; culturing the host cell under conditions such that gp140 is expressed in the cell; and isolating oligomeric gp140 (o-gp140) protein from the host cell. In certain embodiments, the o-gp140 is secreted from the cell and isolated from the cell supernatant.

In a still further aspect, a method of making any of the HIV DNA vaccines described herein is provided. The method comprises the step of combining a nucleic acid expression vector comprising a sequence encoding one or more HIV polypeptides with aseptic PLG microparticles such that the nucleic acid expression vector binds to the PLG microparticles to form a DNA/PLG HIV vaccine. In certain embodiments, the method further comprises the step of lyophilizing the DNA/PLG HIV vaccines.

In another aspect, the invention includes a method of making an HIV protein vaccine as described herein, the method comprising the steps of combining o-gp140 with an adjuvant.

These and other embodiments of the present invention will readily occur to those of ordinary skill in the art in view of the disclosure herein.

BRIEF DESCRIPTION OF THE DRAWINGS

FIG. 1A and FIG. 1B are graphs depicting the effect of PLG microparticles on anti-Gag antibody responses induced by DNA vaccines. FIG. 1A shows geometric mean ELISA titers of animals immunized with plasmid DNA at weeks 0, 4 and 14, then boosted at weeks 38 and 75 with recombinant Env protein formulated with MF59. FIG. 1B shows geometric mean titer of animals immunized with pSINCP DNA at weeks 0, 4 and 14, then boosted at weeks 38 and 75 with recombinant Env protein formulated with MF59. Anti-Gag antibodies are plotted as geometric mean ELISA titer for naked pCMV (solid symbols) and PLG/pCMV (open symbols) and error bars represent SEM.

FIG. 2A and FIG. 2B are graphs depicting the effect of PLG microparticles on anti-Env antibody responses induced by DNA vaccines. FIG. 2A shows geometric mean ELISA titers of animals immunized with plasmid DNA at weeks 0, 4 and 14, then boosted at weeks 38 and 75 with recombinant Env protein formulated with MF59. FIG. 2B shows geometric mean titer of animals immunized with pSINCP DNA at weeks 0, 4 and 14, then boosted at weeks 38 and 75 with recombinant Env protein formulated with MF59. Anti-Env antibodies are plotted as geometric mean ELISA titer for naked pCMV (solid symbols) and PLG/pCMV (open symbols) and error bars represent SEM.

DETAILED DESCRIPTION OF THE INVENTION

Figure 3:
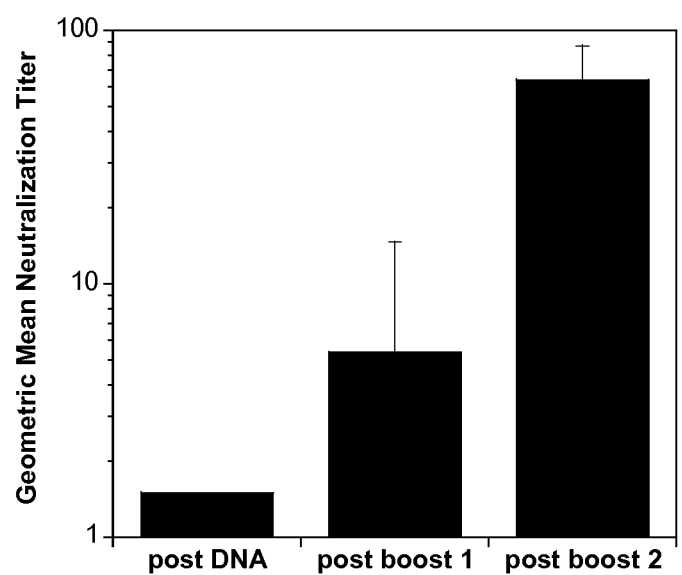
FIG. 3 is a graph depicting geometric mean neutralization titer after DNA administration.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Short Protocols in Molecular Biology,* 4th ed. (Ausubel et al. eds., 1999, John Wiley & Sons); *Molecular Biology Techniques: An Intensive Laboratory Course,* (Ream et al., eds., 1998, Academic Press); *PCR (Introduction to Biotechniques Series)*, 2nd ed. (Newton & Graham eds., 1997, Springer Verlag); Peters and Dalrymple, *Fields Virology* (2d ed), Fields et al. (eds.), B.N. Raven Press, New York, N.Y.

All publications, patents and patent applications cited herein, whether supra or infra, are hereby incorporated by reference in their entireties.

As used in this specification and the appended claims, the singular forms "a," "an" and "the" include plural references unless the content clearly dictates otherwise. Thus, for example, reference to "an antigen" includes a mixture of two or more such antigens.

Prior to setting forth the invention, it may be helpful to an understanding thereof to first set forth definitions of certain terms that will be used hereinafter.

As used herein the term "HIV polypeptide" refers to any HIV peptide from any HIV strain or subtype, including, but not limited to Gag, pol, env, vif, vpr, tat, rev, nef, and/or vpu; functional (e.g., immunogenic) fragments thereof, modified polypeptides thereof and combinations of these fragments and/or modified peptides. Furthermore, an "HIV polypeptide" as defined herein is not limited to a polypeptide having the exact sequence of known HIV polypeptides. Indeed, the HIV genome is in a state of constant flux and contains several domains that exhibit relatively high degrees of variability between isolates. As will become evident herein, all that is important is that the polypeptide has immunogenic characteristics. It is readily apparent that the term encompasses polypeptides from any of the various HIV strains and subtypes. Furthermore, the term encompasses any such HIV protein regardless of the method of production, including those proteins recombinantly and synthetically produced.

Additionally, the term "HIV polypeptide" encompasses proteins that include additional modifications to the native sequence, such as additional internal deletions, additions and substitutions (generally conservative in nature). These modifications may be deliberate, as through site-directed mutagenesis, or may be accidental, such as through naturally occurring mutational events. All of these modifications are encompassed in the present invention so long as the modified HIV polypeptide functions for its intended purpose. Thus, for example, in a vaccine composition, the modifications must be such that immunological activity is not lost. Similarly, if the polypeptides are to be used for diagnostic purposes, such capability must be retained. Thus, the term also includes HIV polypeptides that differ from naturally occurring peptides, for example peptides that include one or more deletions (e.g., variable regions deleted from Env), substitutions and/or insertions. Nonconservative changes are generally substitutions of one of the above amino acids with an amino acid from a different group (e.g., substituting Asn for Glu), or substituting Cys, Met, His, or Pro for any of the above amino acids. Substitutions involving common amino acids are conveniently performed by site specific mutagenesis of an expression vector encoding the desired protein, and subsequent expression of the altered form. One may also alter amino acids by synthetic or semi-synthetic methods. For example, one may convert cysteine or serine residues to selenocysteine by appropriate chemical treatment of the isolated protein. Alternatively, one may incorporate uncommon amino acids in standard in vitro protein synthetic methods. Typically, the total number of residues changed, deleted or added to the native sequence in the mutants will be no more than about 20, preferably no more than about 10, and most preferably no more than about 5.

"Synthetic" polynucleotide sequences, as used herein, refers to HIV-encoding polynucleotides (e.g., Gag- and/or Env-encoding sequences) whose expression has been optimized, for example, by codon substitution and inactivation of inhibitory sequences. See, e.g., U.S. Pat. No. 6,602,705 and International Publications WO 00/39302; WO 02/04493; WO 00/39303; and WO 00/39304 for examples of synthetic HIV-encoding polynucleotides.

"Wild-type" or "native" sequences, as used herein, refers to polypeptide encoding sequences that are essentially as they are found in nature, e.g., Gag and/or Env encoding sequences as found in other isolates such as Type C isolates (e.g., Botswana isolates AF110965, AF110967, AF110968 or AF110975 or South African isolates).

As used herein, the term "virus-like particle" or "VLP" refers to a nonreplicating, viral shell, derived from any of several viruses discussed further below. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, X-ray crystallography, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide that expresses an antigen or antigenic determinant in vivo, such as in gene therapy and DNA immunization applications, is also included in the definition of antigen herein.

For purposes of the present invention, antigens are preferably derived from any subtype of HIV. Antigens can also be derived from any of several known viruses, bacteria, parasites and fungi, or tumor antigens. Furthermore, for purposes of the present invention, an "antigen" refers to a protein that includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts that produce the antigens.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J., and O'Callaghan, C. A., *J. Exp. Med.* 187(9)1367-1371, 1998; Mcheyzer-Williams, M. G., et al, *Immunol. Rev.* 150: 5-21, 1996; Lalvani, A., et al, *J. Exp. Med.* 186:859-865, 1997).

Thus, an immunological response as used herein may be one that stimulates the production of CTLs, and/or the production or activation of helper T-cells. The HIV antigen(s) may also elicit an antibody-mediated immune response. Hence, an immunological response may include one or more of the following effects: the production of antibodies by B-cells; and/or the activation of suppressor T-cells and/or (*T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest. The immunogenic composition can be introduced directly into a recipient subject, such as by injection, inhalation, oral, intranasal and mucosal (e.g., intra-rectally or intra-vaginally) administration.

By "subunit vaccine" is meant a vaccine composition that includes one or more selected antigens but not all antigens, derived from or homologous to, an antigen from a pathogen of interest such as from a virus, bacterium, parasite or fungus. Such a composition is substantially free of intact pathogen cells or pathogenic particles, or the lysate of such cells or particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence that "encodes" a selected polypeptide, is a nucleic acid molecule that is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10-12 nucleotides and up to 5000 nucleotides, and even more preferably 15-20 nucleotides, up to the number of nucleotides present in the full-length sequences described herein (e.g., see the Sequence Listing and claims), including all integer values falling within the above-described ranges.

The polynucleotides described herein include related polynucleotide sequences having about 80% to 100%, greater than 80-85%, preferably greater than 90-92%, more preferably greater than 95%, and most preferably greater than 98% sequence (including all integer values falling within these described ranges) identity to the sequences disclosed herein (for example, to the claimed sequences or other sequences of the present invention) when the sequences of the present invention are used as the query sequence.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra or Ausubel et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., supra or Ausubel et al., supra).

A first polynucleotide is "derived from" second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Purified polynucleotide" refers to a polynucleotide of interest or fragment thereof that is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

"Gene transfer" or "gene delivery" refers to methods or systems for reliably inserting DNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from alphaviruses, pox viruses and vaccinia viruses. When used for immunization, such gene delivery expression vectors may be referred to as vaccines or vaccine vectors.

"T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

Transfer of a "suicide gene" (e.g., a drug-susceptibility gene) to a target cell renders the cell sensitive to compounds or compositions that are relatively nontoxic to normal cells. Moolten, F. L. (1994) *Cancer Gene Ther.* 1:279-287. Examples of suicide genes are thymidine kinase of herpes simplex virus (HSV-tk), cytochrome P450 (Manome et al. (1996) *Gene Therapy* 3:513-520), human deoxycytidine kinase (Manome et al. (1996) *Nature Medicine* 2(5):567-573) and the bacterial enzyme cytosine deaminase (Dong et al. (1996) *Human Gene Therapy* 7:713-720). Cells that express these genes are rendered sensitive to the effects of the relatively nontoxic prodrugs ganciclovir (HSV-tk), cyclophosphamide (cytochrome P450 2B1), cytosine arabinoside (human deoxycytidine kinase) or 5-fluorocytosine (bacterial cytosine deaminase). Culver et al. (1992) *Science* 256:1550-1552, Huber et al. (1994) *Proc. Natl. Acad. Sci. USA* 91:8302-8306.

A "selectable marker" or "reporter marker" refers to a nucleotide sequence included in a gene transfer vector that has no therapeutic activity, but rather is included to allow for simpler preparation, manufacturing, characterization or testing of the gene transfer vector.

A "specific binding agent" refers to a member of a specific binding pair of molecules wherein one of the molecules specifically binds to the second molecule through chemical and/or physical means. One example of a specific binding agent is an antibody directed against a selected antigen.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (i) the prevention of infection or reinfection, as in a traditional vaccine, (ii) the reduction or elimination of symptoms, and/or (iii) the substantial or complete elimination of the pathogen in question. Treatment may be effected prophylactically (prior to infection) or therapeutically (following infection).

"Nucleic acid expression vector" refers to an assembly that is capable of directing the expression of a sequence or gene of interest. The nucleic acid expression vector may include a promoter that is operably linked to the sequences or gene(s) of interest. Other control elements may be present as well. Nucleic acid expression vectors include, but are not limited to, plasmids, viral vectors, alphavirus vectors (e.g., Sindbis), eukaryotic layered vector initiation systems (see, e.g., U.S. Pat. No. 6,342,372), retroviral vectors, adenoviral vectors, adeno-associated virus vectors and the like. See, also, U.S. Pat. No. 6,602,705 for a description of various nucleic acid expression vectors. Expression cassettes may be contained within a nucleic acid expression vector. The vector may also include a bacterial origin of replication, one or more selectable markers, a signal that allows the construct to exist as single-stranded DNA (e.g., a M13 origin of replication), a multiple cloning site, and a "mammalian" origin of replication (e.g., a SV40 or adenovirus origin of replication).

"Packaging cell" refers to a cell that contains those elements necessary for production of infectious recombinant retrovirus that are lacking in a recombinant retroviral vector. Typically, such packaging cells contain one or more expression cassettes which are capable of expressing proteins which encode Gag, pol and env proteins.

"Producer cell" or "vector producing cell" refers to a cell that contains all elements necessary for production of recombinant retroviral vector particles.

In addition, the following is a partial list of abbreviations used herein:

| | |
|---|---|
| µg | microgram |
| AIDS | acquired immune deficiency syndrome |
| APC | antigen presenting cell |
| CCR5 | chemokine receptor 5 |
| CD4+ | cluster of differeniation 4 receptor |
| CD8+ | cluster of differeniation 8 receptor |
| CDC | centers for disease control |
| CHO cells | Chinese hamster ovary cells |
| CMV | cytomegalovirus |
| ConA | Concanvalim A |
| CRF | case report form |
| CRF's | circulating recombinant forms |
| CTAB | cetyltrimetylamnonium bromide |
| CTL | cytotoxic T lymphocyte |
| Cv | cromium |
| DEAE | Diethylaminoethyl |
| DNA | deoxyribonucleic acid |
| DTH | delayed type hypersensitivity |
| ELISA | enzyme-linked immunosorbent assay |
| ELISPOT | enzyme-linked immunospot assay |
| ENV | envelope |
| FIGE | field inversion gel electrophoresis |
| GAG | group-specific antigen |
| GLP | good laboratory practices |
| gp | glycoprotein |
| HAART | highly active antiretroviral therapy |
| HAP | hydroziapatic |
| HBsAg | hepatitis B surface antigen |
| HCV | hepatitis C virus |
| HIV/HIV-1 | human immunodeficiency virus/Type 1 |
| hr | hour |
| HSV | herpes simplex virus |
| IFN | interferon |
| IFNγ | interferon gamma |
| IM | intramuscular |
| IND | investigational new drug |
| IV | intravenous |
| Kb | kilobase |
| kD | kilodalton |
| Kg | kilogram |
| mg | milligram |
| mL | milliliter |
| MF59 | oil-in-water emulsion adjuvant |
| NaCl | sodium chloride |
| NIAID | National Institute of Allergy and Infectious Disease |
| NIH | National Institutes of Health |
| o-or O- | oligomeric |
| PCR | polymerase chain reaction |
| PEG | polyethylene glycol |
| PLG | cationic poly-lactide-coglycolide |
| pSIN | sindbis virus vector |
| PVA | poly(vinyl alcohol) |
| REV | viral protein - involved in regulation of viral expression |
| SAE | serious adverse event |
| SHIV | simian human immunodefiency virus |
| SP resin | modified polyester-carbonate resin |

General Overview

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention relates to methods and compositions for the development of immunogenic compositions (e.g., vaccines) for HIV. For example, an HIV vaccine as described herein may include three or more components. Vaccines as described herein may be intended for intramuscular injection. In certain embodiments, two nucleic acid components are formulated onto (adsorbed onto) cationic poly-lactide-coglycolide (PLG) microparticles and administered as priming immunizations. In addition to the DNA components, a protein composition is also administered in one or more boosting immunizations. The protein component typically comprises at least one HIV polypeptide, for example, a CHO cell-produced, recombinant oligomeric envelope protein with a deletion in the V2 region mixed with the MF-59 adjuvant.

Pharmaceutics Compositions

In a preferred embodiment, the HIV vaccines described herein includes multiple (e.g., three or more) components intended for administration (e.g., intramuscularly) in a 6-9 month, or even longer, time period. The components may be given concurrently or at different time points. For example, two nucleic acid "priming" immunizations may be given, where each priming immunization includes include two separate preparations of DNA encoding Gag protein(s) (e.g., p55 Gag from HIV-1 SF2), and/or Env protein(s) (e.g., an oligomeric, V2-deleted, gp140 envelope protein from HIV-1 SF162), both formulated on PLG microparticles. The nucleic acids will typically be provided separately in unit dose vials containing between 1 µg to 10 mg of DNA and between 10 µg and 100 mg of PLG (e.g., 1 mg of DNA and 25 mg of PLG microparticles). The DNA-containing doses are typically stored in lyophilized form and vials are generally reconstituted in the field. It should be noted that each unit dose vial will typically contain more DNA (or protein) than is actually administered to the patient. The final dosage typically consists of 1 mg in 0.5 mL each of Gag and Env DNA. The DNA components of the vaccine are intended to prime antibody, CD4 and CD8 T cell responses to HIV antigens (e.g., Gag and Env).

As noted above, the immunogenic systems (vaccines) described herein also comprise at least one protein component, typically an HIV polypeptide from any isolate or strain of HIV. For example, in certain embodiments, the protein component comprises a recombinant oligomeric envelope protein from the SF162 strain of HIV-1. Protein monomers of HIV Env may be truncated to an approximate molecular size of 140 kD (e.g., to improve solubility) and the V2 loop may be at least partially removed. The resulting oligomeric molecule resembles the envelope structure of HIV closely. Removal of the V2 variable loop exposes conserved epitopes involved in receptor and/or co-receptor binding. Macaques primed with naked DNA vaccines encoding oligomeric V2-deleted gp140 from the subtype B (CCR5) primary isolate SF162, and boosted with the corresponding recombinant protein, produced antibodies capable of neutralizing a range of distinct subtype B primary isolates. Barnett et al. (2001) *J Virol.* 75(12):5526-40; Srivastava et al. (2002) *J Virol.* (6):2835-47; Srivastava et al. (2003) *J. Virol.* 77(20):11244-11259.

Based on the quantities of passively administered antibodies required to protect macaques and the magnitude and breadth of the neutralization titers seen in macaque studies, suggest that the antibodies induced by vaccines described herein are likely to provide protection from infection in a proportion of animals. Mascola et al. (1999) *J Virol.* 73(5): 4009-18. The amount of protein per does can vary from microgram to milligram amounts. In certain embodiments, the protein is provided such that the dose administered is approximately 100 micrograms in unit dose vials containing envelope protein in sodium citrate buffer, pH 6.0 without preservative.

The protein and/or nucleic acid compositions described herein may also comprise a pharmaceutically acceptable carrier. The carrier should not itself induce the production of antibodies harmful to the host. Pharmaceutically acceptable carriers are well known to those in the art. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee et al. (1997) *J Microencapsul.* 14(2):197-210; O'Hagan et al. (1993) *Vaccine* 11(2):149-54. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc., as well as toxins derived from *E. coli*.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, ethanol, or the like, singly or in combination, as well as substances such as wetting agents, emulsifying agents, or pH buffering agents. Liposomes can also be used as a carrier for a composition of the invention, such liposomes are described above.

Briefly, with regard to viral particles, replication-defective vectors (also referred to above as particles) may be preserved either in crude or purified forms. Preservation methods and conditions are described in U.S. Pat. No. 6,015,694.

Further, the compositions described herein can include various excipients, adjuvants, carriers, auxiliary substances, modulating agents, and the like. Preferably, the compositions will include an amount of the antigen sufficient to mount an immunological response. An appropriate effective amount can be determined by one of skill in the art. Such an amount will fall in a relatively broad range that can be determined through routine trials and will generally be an amount on the order of about 0.1 µg to about 1000 µg (e.g., antigen and/or particle), more preferably about 1 µg to about 300 µg, of particle/antigen.

As noted above, one or more of the components may further comprise one or more adjuvants. Preferred adjuvants to enhance effectiveness include of the composition includes, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59™ (International Publication No. WO 90/14837; Chapter 10 in *Vaccine design: the subunit and adjuvant approach*, eds. Powell & Newman, Plenus Press, 1995), containing 5% Squalene, 0.5% Tween 80, and 0.5% Span 85 (optionally containing various amounts of MTP-PE) formulated into submicron particles using a microfluidizer, (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as QS21 or Stimulon™ (Cambridge Bioscience, Worcester, Mass.) may be used or particle generated therefrom such as ISCOMs (immunostimulating complexes), which ISCOMS may be devoid of additional detergent (see, e.g., WO 00/07621); (4) Complete Freunds Adjuvant (CFA) and Incomplete Freunds Adjuvant (IFA); (5) cytokines, such as interleukins (IL-1, IL-2, IL-4, IL-5, IL-6, IL-7, IL-12 (WO 99/44636), IL16, etc.), interferons (e.g., gamma interferon), macrophage colony stimulating factor (M-CSF), tumor necrosis factor (TNF), beta chemokines (MIP, 1-alpha, 1-beta Rantes, etc.), etc.; (6) monophosphoryl lipids A (MPL) or 3-O-deacylated MPL (3dMPL) e.g., GB-222021, EP-A-0689454, optionally in the substantial absence of alum when used with pneumococcal saccharides e.g., WO 00/56358; (7) combinations of 3dMPL with, for example, QS21 and/or oil-in-water emulsions e.g., EP-A-0835318, EP-A-0735898, EP-A-0761231; (8) oligonucleotides comprising CpG motifs (Roman et al., *Nat. Med.,* 1997, 3:849-854; Weiner et al., *PNAS USA,* 1997, 94:10833-10837; Davis et al. *J. Immunol.,* 1998, 160:870-876; Chu et al., *J. Exp. Med.,* 1997, 186:1623-1631; Lipford et al., *Eur. J Immunol.* 1997, 27:2340-2344; Moldoveanu. et al., *Vaccine,* 1988, 16:1216-1224, Krieg et al., *Nature,* 1995, 3742:546-549; Klinman et al., *PNAS USA,* 1996, 93:2879-2883: Ballas et al., *J Immunol.,* 1996, 157:1840-1845; Cowdery et al., *J Immunol.,* 1996, 156:4570-4575; Halpern et al., *Cell. Immunol.,* 1996, 167:72-78; Yamamoto et al., *Jpn. J Cancer Res.,* 1988, 79:866-873; Stacey et al., *J Immunol,* 1996, 157:2116-2122; Messina et al., *J Immunol.,* 1991, 147: 17591764; Yi et al., *J Immunol.,* 1996, 157:4918-4925; Yi et al., *J Immunol.,* 1996, 157:5394-5402; Yi et al., *J Immunol.,* 1998, 160:4755-4761; and Yi et al., *J Immunol.,* 1998, 1605: 5898-5906; International patent applications WO96/02555, WO98/16247, WO98/18810, WO98/401005 WO98/55495, WO98/37919 and WO98/52581) i.e. containing at least one CG dinucleotide, with 5 methylcytosine optionally being used in place of cytosine; (8) a polyoxyethylene ether or a polyoxyethylone ester e.g. WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g., a CpG oligonucleotide) (WO 00/62800); (11) an immunostimulant and a particle of metal salt e.g. WO 00/23105; (12) a saponin and oil-in-water emulsion e.g., WO 99/11241; (13) a saponin (e.g., QS21)+3dMPL=IL-12 (optionally+a sterol) e.g., WO 98/57659; (14) other substances that act as immunostimulating agents to enhance the effectiveness of the composition. Alum (especially aluminum phosphate and/or hydroxide) and MF59™ are preferred.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

Administration of the pharmaceutical compositions described herein may be by any suitable route (see, e.g., Section C). Particularly preferred is intramuscular or mucosal (e.g., rectal and/or vaginal) administration. Dosage treatment may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1 to 6 months for a second dose, and if needed, a subsequent dose(s) after several months. The dosage regimen will also, at least in part, be determined by the potency of the modality, the vaccine delivery employed, the need of the subject and be dependent on the judgment of the practitioner.

In certain embodiments, the protein component is mixed before administration with a proprietary oil-in-water emulsion adjuvant, MF59C.1 (hereafter referred to as MF59) (See, e.g., International Publication No. WO 90/14837). Various subunit antigens (e.g., HCV E2, HIV gp120, HBsAg, CMV gB, and HSV 2 gD) have been combined with MF59 adjuvant and administered to over 18,000 human subjects to date with an excellent safety and tolerability profile. The protein booster is intended to amplify the primary antibody and CD4+ T cell responses in breadth and duration and to provide a balanced response in both the humoral and cellular compartments of the immune system, capable to achieve the prevention of HIV-1 infection.

As noted above, MF59 adjuvant has been extensively evaluated in clinical trials with a number of different subunit antigens, including those derived from influenza, herpes simplex virus 2 (HSV), human immunodeficiency virus (HIV), cytomegalovirus (CMV), and hepatitis B virus (HBV) and is generally well tolerated with minimal local and systemic adverse reactions that are transient and of mild-to-moderate severity. Over 12,000 subjects have received influenza virus vaccines combined with MF59 adjuvant emulsion in more than 30 clinical studies. Only two patients had serious adverse effects. Moreover, the incidence of adverse effects depend upon the antigen used.

Prime-Boost Regimes

In certain embodiments, multiple administrations (e.g., prime-boost type administration) will be advantageously employed. For example, nucleic acid constructs expressing one or more HIV antigen(s) of interest are administered. Subsequently, the same and/or different HIV antigen(s) are administered, for example in compositions comprising the polypeptide antigen(s) and a suitable adjuvant. Alternatively, antigens are administered prior to the DNA. Multiple polypeptide and multiple nucleic acid administrations (in any order) may also be employed.

As described herein, one exemplary prime-boost regime described herein includes two or more administrations of DNAs encoding one or more HIV antigens followed by one or more administrations of HIV polypeptide antigens themselves. For example, two or more administrations of HIV Gag and HIV Env DNA/PLG compositions (e.g., separate Gag and Env) may be followed by one or more administration of HIV Env protein. HIV-1 DNA constructs are able to stimulate the cellular and humoral arms of the immune system and elicit immune responses capable of preventing HIV-1 infection in chimpanzees. Boyer et al. (1997) *Nat Med* 3:526-532. Adsorption of DNA onto the surface of PLG microparticles improves DNA uptake by the antigen presenting cells (APCs), and enhance cellular and humoral immune responses. O'Hagan et al. (2001) *J Virol.* 75(19):9037-43. PLG is particularly preferred to deliver DNA because the polymer is biodegradable, biocompatible and has been used to develop several drug delivery systems. Okada et al. (1997) *Adv Drug Deliv Rev* 28(1):43-70. In certain embodiments, the ratio of DNA:PLG is between about 1 and 16 w/w % (or any value therebetween).

The "booster" component comprises an HIV protein from any HIV strain or subtype, for example a recombinant oligomeric envelope protein from the subtype B strain (e.g., SF2, SF162, etc.) and/or subtype C strain (Botswana strains and/or South African strains such as TV1). See, e.g., Scriba et al. (2001) *AIDS Res Hum Retroviruses* 17(8):775-81; Scriba et al. (2002) *AIDS Res Hum Retroviruses* 18(2):149-59; Treurnicht et al. (2002) *J Med Virol.* 68(2):141-6. The protein monomers of the Env protein may be truncated and the V2 loop partially removed to increase the exposure of conserved epitopes that are more efficient to elicit cross-reactive neutralizing antibody. Without being bound by one theory, it appears that the protein booster is intended to amplify the primary antibody and CD4+ T cell responses in breadth and duration. Barnett et al. (2001) *J Virol* 75(12):5526-40; Cherpelis et al. (2001) *J. Virol.* 75(3):1547-50. The concentration of protein in each dose may vary from approximately 1 µg to over 1000 µg (or any value therebetween), preferably between about 10 µg and 500 µg, and even more preferably between about 30 µg and 300 µg.

To date, HIV vaccines as described herein have demonstrated a strong record of safety in preclinical studies and clinical trials. See, also, Example 4 below. No evidence of vaccine-related immunodeficiency has been reported. Toxicology studies conducted in mice and rabbits with the HIV vaccine demonstrated that the vaccine was very well tolerated. Findings were consistent with studies conducted with other viral subunit vaccines or with MF59 adjuvant. Reversible local (intramuscular) inflammation is the only notable change seen with such vaccines (see Example 4).

The goal of the HIV vaccine development program is to demonstrate the safety and efficacy of a novel DNA-prime plus recombinant protein-boost HIV vaccine, that is capable of eliciting a combination of broad humoral and cellular responses, and preventing HIV infection or the development of advanced HIV disease/AIDS.

Sources of HIV Antigens

Polynucleotide sequences (e.g., for use in nucleic acid expression constructs) can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge, *Nature* (1981) 292:756; Nambair et al., *Science* (1984) 223: 1299; Jay et al., *J. Biol. Chem.* (1984) 259:6311; Stemmer, W. P. C., (1995) *Gene* 164:49-53.

Next, the gene sequence encoding the desired antigen can be inserted into a vector as described for example, in U.S. Pat. No. 6,602,705 and International Patent Publications WO 00/39302; WO 02/04493; WO 00/39303; and WO 00/39304, which describe suitable exemplary nucleic acid expression vectors and methods of obtaining additional vectors useful in the compositions and methods, described herein.

Expression constructs (e.g., plasmids) typically include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5* to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Furthermore, HIV polypeptide-encoding nucleic acids can be constructed which include a chimeric antigen-coding gene sequences, encoding, e.g., multiple antigens/epitopes of interest, for example derived from one or more viral isolates. Alternatively, multi-cistronic cassettes (e.g., bi-cistronic cassettes) can be constructed allowing expression of multiple antigens from a single mRNA using the EMCV IRES, or the like.

Further, the HIV antigens (and polynucleotides encoding these antigens) used in the claimed formulations may be obtained from one or more subtypes of HIV. There are three distinct branches in the phylogenetic tree of HIV-1 sequences, among these, the M (main) viruses account for almost all of the human infections worldwide. The M-group viruses have been divided into 9 distinct genetic subtypes or clades (A through K). Worldwide, the subtypes A and C account for most of the infections, these subtypes are most common in southern Africa and India, The subtype B is dominant in the American continent, Australia and Europe. Malim et al. (2001) *Cell* 104(4): 469-72. These subtypes are followed in frequency by newer circulating recombinant forms (CRFs). HIV-1 displays an unprecedented genetic diversity within a subtype and even within a single individual. Kwong et al. (2000) *J Virol.* 74(4): 1961-72. This diversity is simply enormous when compared to the diversity found in viruses for which effective vaccines have been developed. Moore et al. (2001) *J Virol.* 75(13): 5721-9. Thus, though vaccines described herein are typically developed based on dominant genetic subtypes, for HIV, effective vaccines against a specific subtype can be readily generated using the teachings herein.

Industrial Applicability

The discovery that HIV was the etiological agent of AIDS in 1983-84 raised hopes for the rapid development of a vaccine. More than 40 candidate HIV vaccines have already been tested in phase I and II clinical trials, and the first phase II trials are now under way in the United States and Thailand. Esparza, J. (2001) *Bull World Health Organ.* 79(12): 1133-7. However, a major impediment for the development of the vaccine has been the lack of scientific evidence on the immunological correlates of protection against HIV and AIDS. Clerici et al. (1996) *Immunol Lett* 51(1-2):69-73. Even though most HIV infected individuals develop broad immunological responses against the virus, these responses are incapable of eliminating the infection or preventing disease progression. This problem is further complicated by the fact that HIV strains vary significantly in different parts of the world. HIV exhibits extensive genetic sequence heterogeneity, particularly in the genes encoding for viral envelope proteins. Different subtype viruses can combine among themselves, generating additional circulating recombinant forms (CRFs). McCutchan et al. (1996) *J. Virol.* 70(6):3331-3338.

Using vaccination to induce a specific anti HIV-1 immune response that is more effective than the natural response to the HIV-1 infection has proven difficult to achieve. In most of the infections for which vaccines are effective, viremia or bacteremia is a critical phase that permits the immune system to contain the pathogen before it reaches the target organ. Ada et al. (2001) *New Engl. J Med.* 345:1042-1053. Thus, it has been postulated that the lack of adequate immune control of HIV-1 is likely due to several factors, including HIV-1's ability to infect and deplete CD4+ cells, the main target during the initial phase of viremia (Greene et al. (2002) *Nat Med.* 8(7): 673-80); HIV-1's ability to mutate the sequence of its surface antigens rapidly; the fact that HIV-1 is a weak immunogen that has the ability to mask surface epitopes that would otherwise be recognized by neutralizing antibodies; and/or the fact that HIV can evade cellular immune responses and establish latent infection at sites that are inaccessible to the immune system (Gotch et al. (2000) *Curr Opin Infect Dis* 13(1):13-17).

Further, although most licensed vaccines elicit both cellular and antibody responses, little is understood about how these known vaccines actually protect against infection. It has been postulated that functional antibody responses can eliminate the inoculum either by killing bacteria, inactivating viruses or neutralizing toxins. Plotkin et al. (2001) *Pediatr Infect Dis J.* 20(1):63-75. However, previously, the HIV vaccines tested have not been able to elicit adequate titers of HIV-1 specific broad neutralizing antibodies against diverse primary isolates of HIV-1.

Among the scientific community, there is general agreement that in order to be successful, an HIV/AIDS vaccine should i) induce antibodies able to neutralize a broad range of primary isolates, ii) induce a durable CD8+ mediated cytotoxic response against a variety of strains, and iii) induce a strong CD4+ T cell response to sustain the CTL activity. See, e.g., Mascola et al. (1999) *J Virol* 73(5): 4009-18. Passively administered antibodies alone can protect macaques against both mucosal and IV challenges with pathogenic SHIV. See, e.g., Mascola et al. (2001) *Curr Opin Immunol* 13(4):489-95. There is, however, skepticism that broadly cross-reactive neutralizing antibodies can be elicited in humans by immunization. This has led some investigators to abandon efforts to include envelope in their vaccines and promote vaccines that rely exclusively on cellular immunity for protection. See, also, Kaul et al. (2001) *J Clin Invest* 107(3): 341-9). However, such vaccines are unlikely to protect from infection and may be expected to limit disease progression.

Thus, the compositions and methods described herein preferably elicit a combination of humoral (neutralizing antibody) and cellular (CD4+ T cells and CD8+ T Cells) responses, although humoral or cellular responses individually may be sufficient. The priming regimen is preferably based on nucleic acid vectors (e.g., pCMV or pSIN) that comprise Gag and/or Env HIV genes, respectively. DNA-based vaccines are attractive because they are flexible and relatively simple to produce. Their distribution may be simplified because DNA itself is very durable when properly stored. Immunization with DNA encoding antigenic proteins elicits both antibody and cell-mediated immune responses. DNA immunization has provided protective immunity in various animal models. See, e.g., Donnelly et al. (1997) *Life Sci.* 60(3):163-72. A DNA vaccine encoding a malaria antigen was tolerated relatively well by 20 volunteers, with only few and mild local reactogenicity and systemic symptoms. Wang et al. (1998) *Science* 282(5388):476-80. A DNA-based vaccine containing HIV-1 Env and Rev genes was administered to 15 asymptomatic HIV-infected patients who were not using antiviral drugs. The vaccine induced no local or systemic reactions, and no laboratory abnormalities were detected. Specifically, no patient developed autoimmune antibodies. MacGregor et al. (1998) *J Infect Dis* 178(1):92-100. Ongoing Phase 1 clinical trials show that therapeutic vaccinations indeed boost anti-HIV-1 immune responses in humans. Ugen et al. (1998) *Vaccine* 16(19):1818-21.

The boost component of the compositions and methods described herein typically includes an HIV protein (e.g., a HIV envelope gp140 protein that has a deletion of the V2 loop, thus exposing conserved epitopes). The HIV protein vaccines described herein generally comprise subunit recombinant antigens and are predicted to be both well tolerated and immunogenic (humoral and cellular) in view of the safety and efficacy date obtained with non-recombinant HIV protein vaccines.

Formulations and Administration

As noted above, the compositions are preferably administered using a "prime-boost" approach, for example, two priming injections (e.g., each including two separate preparations of DNA encoding p55 Gag from HIV-1 SF2, and oligomeric, V2 loop-deleted, gp140 envelope protein from HIV-1 SF162, both formulated on PLG microparticles (Env or Gag PLG/DNA)) are administered. The boost composition comprises a protein, for example an antigen is composed of a recombinant oligomeric, V2 loop-deleted, gp140 envelope protein (HIV o-gp140) in combination with MF59 adjuvant. The protein is typically mixed with the adjuvant shortly before injection.

The DNA vaccines may be provided in 5.0 mL Type I glass vials containing 1.4 mg of DNA and 35 mg of PLG microparticles per vial, in lyophilized form. HIV o-gp140 antigen is supplied as a liquid in 3-mL Type I glass vials containing 140 µg in 0.35 mL/vial. MF59 adjuvant is supplied in 3-mL Type I glass vials containing 0.7 mL/vial. Generally, the dose of DNA and protein actually administered to the subject is less than contained in the vial, for example approximately 1.0 mg of DNA is typically administered to the subject when the vial contains 1.4 mg. Similarly, approximately 100 µg of protein is typically administered to the subject when each unit dose vial contains 140 µg of protein.

Any suitable delivery mode can be used for the nucleic acids and polypeptides. Liposomes can also be used for delivery of these molecules. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527. Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., *Proc. Natl. Acad. Sci. USA* (1987) 84:7413-7416); mRNA (Malone et al., *Proc. Natl. Acad. Sci. USA* (1989) 86:6077-6081); and purified transcription factors (Debs et al., *J. Biol. Chem.* (1990) 265:10189-10192), in functional form. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include (DDAB/DOPE) and DOTAP/DOPE (Boerhinger).

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The DNA and/or protein antigen(s) can also be delivered in cochleate lipid compositions similar to those described by Papahadjopoulos et al., *Biochem. Biophys. Acta.* (1975) 394: 483-491. See, also, U.S. Pat. Nos. 4,663,161 and 4,871,488.

The vaccine components may also be encapsulated, adsorbed to, or associated with, particulate carriers. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J Microencapsul.* 14(2):197-210, 1997; O'Hagan D T, et al., *Vaccine* 11(2):149-54, 1993. Suitable microparticles may also be manufactured in the presence of charged detergents, such as anionic or cationic detergents, to yield microparticles with a surface having a net negative or a net positive charge. For example, microparticles manufactured with anionic detergents, such as hexadecyltrimethylammonium bromide (CTAB), i.e. CTAB-PLG microparticles, adsorb negatively charged macromolecules, such as DNA. (see, e.g., Int'l Application Number PCT/US99/17308). Methods of making and using PLG particles to deliver nucleic acids are described in International Patent Publications WO 98/33487; WO 00/06123; WO 02/26212; and WO 02/26209.

Polymers such as polylysine, polyarginine, polyornithine, spermine, spermidine, as well as conjugates of these molecules, may also be used for transferring a nucleic acid of interest.

Additionally, biolistic delivery systems employing particulate carriers such as gold and tungsten, are especially useful for delivering nucleic acid vectors of the present invention. The particles are coated with the nucleic acid(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

Also, needle-less injection systems can be used (Davis, H. L., et al, *Vaccine* 12:1503-1509, 1994; Bioject, Inc., Portland, Oreg.).

The compositions described herein may either be prophylactic (to prevent infection) or therapeutic (to treat disease after infection). The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, and the like, may be present in such vehicles. Certain facilitators of nucleic acid uptake and/or expression can also be included in the compositions or coadministered, such as, but not limited to, bupivacaine, cardiotoxin and sucrose.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) (with or without the corresponding antigen) in liposomes, and direct microinjection of the DNA into nuclei.

Direct delivery of polynucleoides and polypeptides in vivo will generally be accomplished, as described herein, by injection using either a conventional syringe or a gene gun, such as the Accell® gene delivery system (PowderJect Technologies, Inc., Oxford, England). The constructs can be injected either subcutaneously, epidermally, intradermally, intramucosally such as nasally, rectally and vaginally, intraperitoneally, intravenously, orally or, preferably, intramuscularly. Dosage treatment may be a single dose schedule or a multiple dose schedule. Administration of nucleic acids may also be combined with administration of peptides or other substances.

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXPERIMENTAL

Example 1

Vaccine Manufacturing Process and Release

A. PLG/DNA HIV Vaccines

For PLG/DNA priming immunization with nucleic acid, plasmid DNA (Env or Gag) was adsorbed onto biodegradable polymer microparticles (PLG) essentially as follows. To manufacture the DNA vaccines, *E. coli* (strain DH5) was transformed with plasmids encoding the HIV Env and Gag genes. A modified alkaline lysis method was used to isolate plasmid DNA from chromosomal DNA, proteins, and other cellular debris. Plasmid DNA was concentrated by precipitation using PEG 8000. The plasmids were then purified by two chromatography steps and transferred by ultrafiltration into formulation buffer.

PLG microparticles were produced by an aseptic manufacturing process. See, e.g., U.S. Pat. Nos. 5,603,960; 6,534,064 and 6,573,238; Gupta et al. (1998) *Adv Drug Deliv Rev.* 32(3):225-246; O'Hagan (1998) *J Pharm Pharmacol.* 50(1):1-10. In particular, PLG (dissolved in methylene chloride) was homogenized with formulation buffer and CTAB (cation surfactant) solution under high speed and high shear of mixing to form a stable emulsion. The removal of methylene chloride by nitrogen purge causes PLG to form microparticles, due to the tendency of the cationic surfactant to stay at the PLG interface. These positively charged microparticles bind with negatively charged DNA to form the PLG/DNA immunogen.

B. HIV o-gp140 Antigen

The recombinant, oligomeric HIV gp-140 (o-gp140) was prepared essentially as described in Srivastava et al. (2003) *J. Virol.* 77(20):11244-11259. Following fermentation of the host cells, the cell culture supernatant was harvested, filtered, concentrated, and purified.

The purified o-gp140 protein fraction was further treated to remove adventitious viruses. The first of these steps was viral inactivation at pH 3.5 for 1 hour. The sample was then concentrated and diafiltered into a buffer at pH 4 in preparation for cation capture using SP resin, which captures o-gp140 and allows many viruses to flow through. The o-gp140 was eluted, concentrated and diafiltered into formulation buffer. This formulated bulk product was then filtered through a Ultipor® VF grade DV50 virus removal membrane followed by filtration through a 0.2 µm membrane.

C. MF59 Adjuvant

MF59 adjuvant (MF59C.1) is an oil-in-water emulsion with a squalene internal oil phase and a citrate buffer external aqueous phase. See, e.g., U.S. Pat. Nos. 6,299,884 and 6,086,901; Ott et al. "MF59—Design and Evaluation of a Safe and Potent Adjuvant for Human Vaccines," Vaccine Design: The Subunit and Adjuvant Approach (Powell, M. F. and Newman, M. J. eds.) Plenum Press, New York, pp. 277-296 (1995). Two nonionic surfactants, sorbitan trioleate and polysorbate 80, serve to stabililize the emulsion. The safety of the MF59 adjuvant has been demonstrated in animals and in humans in combination with a number of antigens. See, e.g., Higgins et al., "MF59 Adjuvant Enhances the Immunogenicity of Influenza Vaccine in Both Young and Old Mice," Vaccine 14(6):478-484 (1996).

Example 2

Vaccine Composition

The components of the PLG/DNA priming vaccines, o-gp140 boost antigen, and MF59 adjuvant are provided in the following tables.

TABLE 1

PLG DNA (Env) Vaccine Composition

| Component | Quantity per mL* | Quantity per dose (maximum dose) |
|---|---|---|
| Poly (D.L-Lactide-co-glycolide) | 50.0 mg | 25.0 mg |
| Plasmid DNA (Env) | 2.0 mg | 1.0 mg |
| Hexadecyltrimethylammonium Bromide | 0.5 mg | 0.25 mg |
| Mannitol, USP, EP | 44 mg | 22 mg |
| Sucrose, USP/NF | 14.7 mg | 7.35 mg |
| EDTA, Disodium salt Dihydrate, USP | 0.37 mg | 0.28 mg |
| Sodium Citrate Dihydrate, USP/EP | 1.4 mg | 1.10 mg |
| Citric Acid Monohydrate, USP/EP | 0.04 mg | 0.02 mg |
| Water for Injection | qs | qs |

*following reconstitution

TABLE 2

PLG DNA (Gag) Vaccine Composition

| Component | Quantity per mL* | Quantity per dose (maximum dose) |
|---|---|---|
| Poly (D.L-Lactide-co-glycolide) | 50.0 mg | 25.0 mg |
| Plasmid DNA (Gag) | 2.0 mg | 1.0 mg |
| Hexadecyltrimethylammonium Bromide | 0.5 mg | 0.25 mg |
| Mannitol, USP, EP | 44 mg | 22 mg |
| Sucrose, USP/NF | 14.7 mg | 7.35 mg |
| EDTA, Disodium salt Dihydrate, USP | 0.37 mg | 0.18 mg |
| Sodium Citrate Dihydrate, USP/EP | 1.4 mg | 0.70 mg |
| Citric Acid Monohydrate, USP/EP | 0.04 mg | 0.02 mg |
| Water for Injection | qs | qs |

*following reconstitution

TABLE 3

HIV o-gp140 Antigen Composition

| Component | Quantity per mL | Quantity per dose (100 µg) |
|---|---|---|
| o-gp140 | 0.4 mg | 0.1 mg |
| Sodium citrate, dihydrate | 2.75 mg | 0.69 mg |
| Citric acid, monohydrate | 0.15 mg | 0.04 mg |
| Sodium chloride | 17.53 mg | 4.38 mg |
| Water for Injection | qs | qs |

TABLE 4

MF59C.1 Adjuvant Composition

| Component | Quantity per mL | Quantity per dose |
|---|---|---|
| Squalene | 39 mg | 9.75 mg |
| Polysorbate 80 | 4.7 mg | 1.18 mg |
| Sorbitan trioleate | 4.7 mg | 1.18 mg |
| Sodium citrate, dihydrate, USP | 2.68 mg | 0.66 mg |
| Citric acid, monohydrate, USP | 0.17 mg | 0.04 mg |
| Water for Injection | qs | qs |

The schedule for vaccination injections is to inject at multiple time points (e.g., at 5 or 6 different time points), administered at 0, 1, 2, 6, 9 and possibly 12 months. Several immunization schedules are evaluated to maximize the immune response. These schedules may include vaccinations at 4 or 5 timepoints, according to any schedule, for example as set forth below. All vaccinations will be administered by intramuscular injection in the outpatient setting. Table 5 shows an exemplary immunization protocol.

TABLE 5

Protocol Of Immunization
STUDY AGENTS
A: Clade B Gag + Env DNA/PLG microparticles, dose indicated below
B: Clade B gp140 Env protein, 100 µg

| # | DNA Dose Gag/Env (µg) | Protein Dose | 0 (0) | 1 (28) | 2 (56) | 4 (112) | 6 (168) | 9 (236) | 12* (365) |
|---|---|---|---|---|---|---|---|---|---|
| 1 | 1000/1000 | 100 µg | A | A | A |   | B | B | B |
| 2 | 1000/1000 | 100 µg | A | A |   |   | A + B | B | B |
| 3 | 1000/1000 | 100 µg | A | A |   | A + B | B |   | B |
| 4 | 1000/1000 | 100 µg | A | A |   |   | B | B | B | schedule
*If needed to sustain an immunologic response

Example 3

Handling and Storage

To prepare the DNA/PLG vaccine for administration, one vial of each DNA/PLG (Env or Gag) is reconstituted by drawing 0.7 mL Water for Injection into a syringe and adding it to each of the two vials. The vials are swirled vigorously for up to two minutes. The mixing is complete when the suspensions appear uniform, milky, and fully dispersed. The reconstituted solutions are administered without further preparation to deliver the highest DNA/PLG dose (1000 µg). To prepare the 500-µg, and 250-µg doses, use a new syringe to add an additional 0.7 mL or 2.1 mL of 0.9% NaCl solution (Normal Saline), respectively, to the all ready reconstituted vials, and swirl to mix. Using a new syringe, draw up 0.5 mL of the Env PLG/DNA mixture, and then 0.5 mL of the Gag DNA/PLG mixture, into the same syringe. The total DNA dose, in a combined volume of 1 mL, can then be administered intramuscularly (IM) into the deltoid muscle.

HIV o-gp140 antigen will be mixed before administration with MF59 adjuvant. To prepare the vaccine dose for administration, mix the contents of the MF59 vial by repeated gentle swirling and inversion (not vigorous shaking) and then withdraw 0.35 mL into a 1-mL sterile syringe. Inject this adjuvant into the 3 mL vial containing the thawed HIV o-gp 140 antigen and mix by gentle swirling. Use a new syringe to draw up 0.5 mL of the mixture, which can then be administered intramuscularly (IM) into the deltoid. The final vaccine has a milky white opacity. The injection should be given shortly after addition of the adjuvant.

The thawed HIV o-gp140 antigen is stable at 2° to 8° C. for 8 hours. Antigen that has been thawed for over 8 hours (even with refrigeration), is not preferred, as it may have reduced potency.

Individuals receiving placebo will receive 0.5 mL of calcium- and magnesium-free phosphate-buffered saline. Supplied as a clear, colorless solution in vials containing a volume to deliver a 1 mL dose. The vials must be stored in a refrigerator at 2 to 8° C.

A. Vaccine Storage Conditions

The lyophilized DNA/PLG vaccines are stored at 2-8° C. HIV o-gp140 are stored frozen below −60° C. and the MF59 adjuvant is stored in a refrigerator at 2° to 8° C. MF59 should not be frozen.

Example 4

Animal Studies

A nonclinical safety assessment program was designed to support the clinical administration of three intramuscular (IM) doses of the HIV DNA vaccine formulation followed by three IM doses of the HIV Protein vaccine formulation. One clinical dose (1.0 mL) of the DNA vaccine formulation contains 1 mg Env-DNA, 1 mg Gag-DNA, and 50 mg PLG whereas one clinical dose (0.5 mL) of the HIV Protein Vaccine contains 0.1 mg/0.25 mL Env protein plus 0.25 mL MF59.

The following GLP studies were conducted to assess whether integration into host genomic DNA occurs and to characterize tissue localization and persistence of the HIV DNA vaccine formulation when administered as a single IM injection to New Zealand White rabbits and BALB/c mice, respectively. These studies are further described below in Section A titled "An Integration Study with DNA-PLG Formulations after a Single Intramuscular Injection to New Zealand White Rabbits" and Section B titled "Single Dose Biodistribution Study of HIV DNA Vaccine Formulations in BALB/c Mice."

As described in further detail below, in these studies, toxicity was evaluated based on viability, clinical observations, body weights, and macroscopic postmortem examinations. Physical examinations and dermal scoring of injection sites were also performed in the mouse biodistribution study. Results of these studies demonstrated that administration of a single dose of the Env-DNA vaccine formulation resulted in no integration into the rabbit genomic DNA and good tolerability in New Zealand White rabbits and BALB/c mice. The analysis of mouse tissues for distribution of the HIV DNA vaccine formulation was also performed.

In addition, the following GLP toxicology study was conducted to assess the systemic and local tolerability of the HIV vaccine formulation when administered to New Zealand White rabbits via IM injection. (See, Section C below, titled "Multiple-Dose Intramuscular Injection Toxicity Study with HIV DNA Vaccine Formulation in New Zealand White Rabbits"). In this study, animals received four doses, two weeks apart, of the HIV DNA vaccine formulation followed by four doses, two weeks apart, of the HIV Protein vaccine formulation. The first HIV Protein vaccine dose was administered on the same day as the last HIV DNA vaccine dose. A recovery period of two weeks was included in the study design. Rabbits received the planned clinical dose (1 mL HIV DNA vaccine/dose; 0.5 mL HIV Protein vaccine/dose) by the clinical route of administration (IM). However, rabbits received four doses each of the HIV DNA vaccine and the HIV Protein vaccine, exceeding the intended clinical regimen (three doses each) by one dose. The rabbit dosing regimen was condensed relative to the clinical regimen (monthly), however, rabbit immunogenicity studies have demonstrated that an every two-week regimen is appropriate from an immunological standpoint.

In this study, toxicity was evaluated based on clinical signs, dermal scoring of injection sites, body weights and temperatures, food consumption, ophthalmoscopy, clinical pathology (hematology, serum chemistry, and coagulation including fibrinogen), organ weights, and macroscopic postmortem and histopathological examinations. Analysis of serum for antibodies (anti-nuclear and Env- and Gag-antibodies) was also performed. Under the conditions of this study and based on the available preliminary data (terminal organ weights, macroscopic evaluation and histology pending), no systemic or local effects related to the administration of the HIV vaccine formulation were identified.

The safety and persistence at the injection site of the HIV DNA vaccine formulation was further assessed in the following non-GLP studies, described in further detail below in Section D titled "Exploratory DNA/PLG Local Irritation Tolerance Study in Male New Zealand White Rabbits" and Section E titled "Single Dose Intramuscular and Multiple-Dose (Two) Mouse Immunogenicity Study with PCR Injection Site Assessment."

The single dose study was conducted to evaluate the potential local irritant effects of various concentrations of DNA/PLG in New Zealand White male rabbits when administered by a single IM injection. Potential toxicity was evaluated based on clinical signs, dermal scoring of injection sites, body weight, comprehensive macroscopic examination, and microscopic evaluation of injection sites. Under the conditions of this study, various concentrations of DNA/PLG were well tolerated when administered to male New Zealand White rabbits as a single IM injection.

The multiple-dose immunogenicity study assessed the presence of Gag-DNA PLG at the IM injection site four and eight weeks post-last dose in female BALB/c mice that received two administrations (Days 0 and 28) of Gag-DNA PLG formulations. Results demonstrated that the PLG formulations were comparable to a naked-DNA control with regard to persistence and that the amount remaining in the injection site 4 and 8 weeks post-last dose was insignificant (approximately $10^{-7}$% of the infected amount).

A. An Integration Study with DNA-PLG Formulations after a Single Intramuscular Injection to New Zealand White Rabbits To assess the integration of the HIV DNA-PLG vaccine formulation (Env-DNA PLG and Gag-DNA PLG) into the host genomic DNA when administered via a single IM injection to New Zealand White rabbits the following studies were performed. The study consisted of three groups of 2 animals/sex/group. On Day 0, treated rabbits received a single IM injection (0.5 mL/leg) of either the Env-DNA PLG or the Gag-DNA PLG in each hind leg. (See, Table 6). Control rabbits received no injection. All animals were necropsied on Day 29.

TABLE 6

Experimental Study Design

| | | | | Number of Animals | | | |
|---|---|---|---|---|---|---|---|
| | | Treatment | | Total | | Necropsy[c] | |
| Group | Material | Dose[a] DNA (mg) | Volume[b] (mL) | M | F | M | F |
| 1 | Control | 0 | 0 | 2 | 2 | 2 | 2 |
| 2 | Env-DNA PLG | 2 | 1 | 2 | 2 | 2 | 2 |
| 3 | Gag-DNA PLG | 2 | 1 | 2 | 2 | 2 | 2 |

[a]Group 2 and 3 animals received a dose of 1 mg DNA, 25 mg PLG/0.5 mL/leg in each hind leg for a total dose/animal of 2 mg DNA, 50 mg PLG. Dosing occurred on Day 0 of the study.
[b]Group 2 and 3 animals received a volume of 0.5 mL/leg for a total volume/animal of 1 mL.
[c]Necropsy was performed 30 days post-dosing (Day 29)

Potential toxicity was evaluated based on viability observations for mortality and general condition, body weights, and a comprehensive postmortem macroscopic examination. In addition, injection sites were collected at necropsy for Polymerase Chain Reaction (PCR) analysis to evaluate the integration of the DNA vaccine into the rabbit genomic DNA. Additional tissues (see Table 7) were also collected for potential PCR analysis in the event of positive integration results at the injection site. For the PCR analysis, DNA was extracted from the rabbit tissue, quantitated, and subjected to field inversion gel electrophoresis (FIGE) to separate the rabbit genomic DNA from the extrachromosomal plasmid DNA. DNA of a size greater than 17 kb was excised and purified from the gel. Both the extracted and the FIGE purified DNAs (1 μg) were analyzed using a quantitative PCR assay to assess the integration of the target sequence (plasmid vector Env-DNA PLG) in each preparation. DNA extracted from tissues of control animals was pooled according to sex; DNA from treated animals was not pooled but analyzed separately.

TABLE 7

Tissues collected for PCR analysis

| | |
|---|---|
| Bone marrow (sternum, femur) | Lungs (with mainstem bronchi) |
| Brain (medulla, pons, cerebrum, cerebellum) | Lymph nodes (submandibular) |
| Kidneys | Ovaries |
| Injection Sites | Spleen |
| Liver | Testes |

There were no deaths and no treatment-related adverse effects on clinical signs and body weights. No treatment related changes were noted in the macroscopic examination either. Results of the PCR integration analysis revealed no integration of the Env-DNA PLG into the host genomic DNA (see Table 8). Because no integration occurred at the injection sites, no additional tissues were evaluated.

TABLE 8

Quantitative PCR assay results of injection sites

| | Env-DNA PLG (copies/μg DNA) | |
|---|---|---|
| SAMPLE | Extracted DNA[a] | FIGE Purified DNA[b] |
| Control Male | LLD | LLD |
| Male # 2020 | 2637 | LLD |
| Male # 2021 | 2364 | LLD |
| Control Female | LLD | LLD |
| Female # 2520 | 33890 | LLD |
| Female # 2521 | 19814 | LLD |

[a]quantification of the target sequence in genomic DNA prior to field inversion gel electrophoresis (extrachromosomal plasmid DNA plus genomic DNA)
[b]quantification of the target sequence in genomic DNA purified by field inversion gel electrophoresis (genomic DNA only)
LLD = lower that the limit of detection of the assay (5 copies/μg DNA)

In conclusion, a single IM dose of either Env-DNA PLG or Gag-DNA PLG containing a total of 2 mg of DNA and 50 mg of PLG were well tolerated in New Zealand White rabbits. No treatment-related adverse effects were noted and no integration of plasmid vector Env-DNA into rabbit genomic DNA obtained from the injection sites was detected.

B. Single Dose Biodistribution Study of HIV DNA Vaccine Formulations in BALB/c Mice To assess the tissue localization and persistence of the HIV DNA PLG vaccine formulations (Env-DNA PLG and Gag-DNA PLG) after a single administration via IM injection to BALB/c mice, the following studies were performed. The study included five groups of 15 animals/sex/group. On Day 1, treated mice received a single IM injection of either a high or a low dose of Env-DNA PLG or Gag-DNA PLG in the right biceps femoris area. Control mice received no injection. Five animals/sex/group were necropsied one week (Day 8), two months (Day 61), or three months (Day 91) post-dosing. (Table 9).

Potential toxicity was evaluated based on viability observations for mortality and general condition, physical examinations, body weights, dermal Drazie scoring of injection sites, and a comprehensive postmortem macroscopic examination. In addition, selected tissues (see Table 10) were collected at each necropsy for PCR analysis to evaluate the biodistribution and persistence of the DNA vaccine into mouse tissues. For the PCR analysis, DNA was extracted from each mouse tissue, quantitated, subjected to PCR amplification using a fluorescence probe, and followed by fluorescence detection. Of the collected tissues, only tissues from the Env-DNA PLG treated rabbits were analyzed.

mg of PLG was well tolerated in BALB/c mice. No treatment-related adverse effects were noted.

C. Multiple-Dose Intramuscular Injection Toxicity Study with HIV DNA Vaccine Formulation in New Zealand White Rabbits To assess the local and systemic toxicity of the HIV Vaccine formulation in New Zealand White rabbits after repeated administration and to determine the reversibility of findings, the following studies were conducted. Two groups of 8 animals/sex/group were used. Treated rabbits received four doses of the HIV DNA vaccine formulation (Env- and Gag-DNA PLG) given every other week followed by four doses of the HIV Protein Vaccine formulation, also given every other week. The last HIV DNA vaccine dose and the first HIV Protein vaccine dose were administered on the same day (Day

TABLE 9

Experimental Study Design

| Group and Treatment | Dose Level[a] | Dose volume (μL/dose)[a] | Total | Day 8 Necropsy | Day 61 Necropsy | Day 91 Necropsy |
|---|---|---|---|---|---|---|
| 1 (Control) None | 0 | 0 | 15 | 5 | 5 | 5 |
| 2 Env-DNA PLG | 10 μg DNA 0.25 mg PLG | 20 | 15 | 5 | 5 | 5 |
| 3 Env-DNA PLG | 100 μg DNA 2.5 mg PLG | 50 | 15 | 5 | 5 | 5 |
| 4 Gag-DNA PLG | 10 μg DNA 0.25 mg PLG | 20 | 15 | 5 | 5 | 5 |
| 5 Gag-DNA PLG | 100 μg DNA 2.5 mg PLG | 50 | 15 | 5 | 5 | 5 |

[a]Dosing occurred on Day 1 of the study.

TABLE 10

Tissues Collected for PCR Analysis

| | |
|---|---|
| Bone marrow (both femurs) | Lung |
| Brain | Lymph nodes (mandibular) |
| Kidneys | Ovaries |
| Injection Site (right biceps femoris) | Spleen |
| Liver | Testes |

There were no deaths that could be associated with administration of the test articles and no treatment-related adverse effects on clinical signs and body weights. No erythema or edema was seen at the injection sites. No treatment related changes were noted in the macroscopic examination.

In conclusion, a single IM dose of either Env-DNA PLG or Gag-DNA PLG containing up to 100 μg of DNA and up to 2.5

43). Doses were administered via IM injections into the quadricep leg muscle and legs were alternated except on Day 43 when both legs were injected. Control animals received four IM injections of saline solution followed by four IM injections of MF59. Four animals/sex/group were necropsied three days (Day 88, main necropsy) or two weeks post-dosing (Day 99, recovery necropsy). Table 11 describes the experimental design.

Potential toxicity was evaluated based on clinical signs, dermal scoring of injection sites, body temperature, body weight, food consumption, ophthalmic examination, clinical pathology (hematology, coagulation, and serum chemistry parameters), terminal organ weights, comprehensive macroscopic examination, and microscopic evaluation of selected tissues.

TABLE 11

Experimental Study Design

| Treatment | 1 | 15 | 29 | 43 | 57 | 71 | 85 | 88 | 99 |
|---|---|---|---|---|---|---|---|---|---|
| GROUP 1[a] Control (dose volume) | | | | | | | | | |
| Saline Control | 1 mL | 1 mL | 1 mL | 1 mL | none | none | none | Main Necropsy[e] | Recovery Necropsy[e] |
| MF59 Control[b] | none | none | none | 0.5 mL | 0.5 mL | 0.5 mL | 0.5 mL | | |
| GROUP 2[a] DNA Vaccine (dose volume) | | | | | | | | | |
| Env- & Gag-DNA PLG[c] | 1st dose (1 mL) | 2nd dose (1 mL) | 3rd dose (1 mL) | 4th dose (1 mL) | none | none | none | | |

TABLE 11-continued

Experimental Study Design

| | DAY OF STUDY | | | | | | | | |
|---|---|---|---|---|---|---|---|---|---|
| Treatment | 1 | 15 | 29 | 43 | 57 | 71 | 85 | 88 | 99 |
| Env Protein Dose[d] | none | none | none | 1st dose (0.5 mL) | 2nd dose (0.5 mL) | 3rd dose (0.5 mL) | 4th dose (0.5 mL) | | |

[a]16 animals (8 M + 8 F)
[c]consists of 0.25 mL of MF59 plus 0.25 mL saline
[c]consists of 0.5 mL Env-DNA PLG (2 mg DNA, 50 mg PLG/mL) plus 0.5 mL Gag-DNA PLG (2 mg DNA, 50 mg PLG/mL)
[d]consists of 0.25 mL of Env Protein (0.4 mg/mL) plus 0.25 mL MF59
[e]4 animals/sex/group The animals were observed twice daily for mortality and morbidity and once daily for signs of toxicity. In addition, detailed observations were made predose, 4 hr post-dose on each dosing day, weekly, and at each necropsy. Injection sites were assessed for signs of irritation and graded based on a modified Draize score prior to dosing and 24 and 48 hr after each injection. Body temperatures were taken pre-treatment, prior to each dose, and 24 hr after each dose. Body weights were recorded pre-treatment, weekly thereafter, and at necropsy. Food consumption was assessed weekly. The ophthalmology evaluation was performed pre-treatment and prior to each necropsy. Blood samples for hematology, serum chemistry, and coagulation (including fibrinogen) analysis were collected pre-treatment, pre-dose on Days 29 and 57, and on Days 87 and 99. Additional blood samples were taken pre-treatment, pre-dose on Days 15, 43, 71, and on Days 87 and 99 for antibody (anti-nuclear and Env- and Gag-antibodies) analysis. At each necropsy, a complete macroscopic examination and microscopic evaluation of selected tissues (see Table 12) were performed. Organ weight data on selected organs (Table 13) were also collected. In addition, selected tissues were collected for possible assessment of distribution of the DNA vaccine into host tissues by PCR analysis (Table 14).

TABLE 12

Histopathology Tissue List

| | |
|---|---|
| Eyes | Kidneys |
| Femur with bone marrow (including knee joint) | Liver |
| Gall Bladder | Lung and bronchi |
| Lesions (if any) | Optic nerve |
| Lymph nodes (inguinal, lumbar, mesenteric, and popliteal) | Spleen |
| Injection Sites | Thymus |

TABLE 13

Organ Weights List

| | | |
|---|---|---|
| Adrenals | Heart | Spleen |
| Brain | Kidneys | Testis |
| Epididymis | Liver | Thymus |
| Gall Bladder | Ovaries | |

TABLE 14

Tissues Collected for Potential PCR Analysis

| | | |
|---|---|---|
| Brain | Spleen | Lung |
| Mandibular lymph node | Liver | Injection Sites |
| Ovaries/Testis | Kidney | Bone marrow |

Preliminary data (up to Day 84) revealed no deaths that could be associated with administration of the test articles and no treatment-related adverse effects on clinical signs, body weights, food consumption, and body temperature. Dermal scoring of the injection sites revealed occasional instances of edema or erythema in a few animals from both the control and treated group. Although the incidence of these dermal irritation reactions was slightly higher in Group 2 (HIV Vaccine treatment) animals, the findings were mild in severity (very slight to slight) and completely resolved by the next observation period. Available preliminary data (up to Day 57) for clinical pathology demonstrated that there were no treatment-related effects on hematology, coagulation, or clinical chemistry parameters.

In conclusion, under the conditions of this study and based on the available preliminary data, no systemic effects related to the administration of the HIV vaccine formulation were identified. Local effects consisted of occasional instances of very slight to slight erythema or edema at the injection sites, which appeared fully resolved by the next observation period. Four IM injections of the HIV DNA vaccine given every other week, followed by four IM injections of the HIV Protein vaccine, also given every other week, were well tolerated by New Zealand White rabbits.

D. Exploratory DNA/PLG Local Irritation Tolerance Study in Male New Zealand White Rabbits—Single Dose Intramuscular To assess the potential local irritant effects of various concentrations of DNA/PLG in New Zealand White male rabbits when administered by a single IM injection, the followings studies were performed using two groups of 9 male rabbits each. On Day 1, each rabbit received a 0.5 mL IM injection of the test and control articles. Three rabbits/group were necropsied one day (Day 2), one week (Day 8), or two weeks post-dosing (Day 15). Experimental design is depicted in Table 15.

Potential toxicity was evaluated based on clinical signs, dermal scoring of injection sites, body weight, comprehensive macroscopic examination, and microscopic evaluation of injection sites.

TABLE 15

Experimental Design

| Group | No of Males | Treatment[a] | | | | Necropsy Day - No. of animals | | |
|---|---|---|---|---|---|---|---|---|
| | | IM Site 1 | IM Site 2 | IM Site 3 | IM Site 4 | 2 | 8 | 15 |
| 1 | 9 | Saline | 100 mg PLG/PVA | 1% DNA + 100 mg PLG (DF) | 1% DNA + 100 mg PLG (RF) | 3 | 3 | 3 |
| 2 | 9 | 0.1% CTBA | 100 mg PLG/PVA | 2% DNA + 50 mg PLG (DF) | 4% DNA + 25 mg PLG (DF) | 3 | 3 | 3 |

[a]Injection volume = 0.5 mL
DF = Development Formulation
RF = Research Formulation There was no mortality and no treatment-related effects on body weight. Apparent bruising of the injection sites was observed sporadically in 4/9 and 5/9 rabbits in Groups 1 and 2, respectively, during days 1-4. Bruising was noted at all injection sites except injection site #2. This finding of slight bruising at the injection sites is consistent with IM injections. Results of the dermal Draize scoring of the injection sites are presented in Table 16. Very slight edema was noted in two Group 1 rabbits (IM sites 3 and 4) on Days 13 to 15 and in one Group 2 rabbit (IM site 4) on Days 13 to 14. Postmortem macroscopic findings were limited to the injection sites and consisted of red firm areas, tan areas, hemorrhage on fascia overlying muscle, and subcutaneous hemorrhagic areas. These findings were more prevalent on Day 2. Histopathological examination of the injection sites revealed the characteristic response to needle trauma (muscle fiber degeneration and hemorrhage) in the saline treated sites. Evaluation of the test article treated sites revealed, on Day 2, minimal to mild treatment-related inflammation that was similar for all formulations. On Day 8, granulomatous changes were the predominant findings and there was no difference between the formulations. These granulomatous changes are consistent with know responses to PLG microspheres and/or the regenerative process. By Day 15, the histological changes were partially [1% DNA+100 mg PLG (development and research formulations), 2% DNA+50 mg PLG, 4% DNA+25 mg PLG] or fully resolved (100 mg PLG/PVA). See, also Table 16.

TABLE 16

Dermal Irritation Results

| Group | Test/Control Article Identification | Findings |
|---|---|---|
| 1 | Saline | None |
| | 100 mg PLG/PVA | None |
| | 1% DNA + 100 mg PLG (DF) | Very slight edema in 1 rabbit on Days 13-15. |
| | 1% DNA + 100 mg PLG (RF) | Very slight edema in 1 rabbit on Days 13-15. |

TABLE 16-continued

Dermal Irritation Results

| Group | Test/Control Article Identification | Findings |
|---|---|---|
| 2 | 0.1% CTAB | None |
| | 100 mg PLG/PVA | None |
| | 2% DNA + 50 mg PLG (DF) | None |
| | 4% DNA + 25 mg PLG (DF) | Very slight edema in 1 rabbit on Days 13-14. |

DF = Development Formulation
RF = Research Formulation

In conclusion, various concentrations of DNA/PLG were well tolerated when administered to male New Zealand White rabbits as a single IM injection. Injection site findings were most frequent/strongest (mild to minimal) on day 2 and were partially to fully resolved by the end of the recovery period.

E. Multiple-Dose (Two) Mouse Immunogenicity Study with PCR Injection Site Assessment To assess immunogenicity and persistence of Gag-DNA PLG formulations at the IM injection sites, ten female BALB/c mice per group were treated as outlined in Table 17. Animals were dosed on days 0 and 28 and IM injection sites were harvested 4 and 8 weeks post-last dose. The formulations tested in this study were similar to the formulation used in the toxicology studies.

TABLE 17

Experimental Design

| Group | No of mice | Treatment[a] | Necropsy - No of mice | |
|---|---|---|---|---|
| | | | Main[b] | Recovery[c] |
| 1 | 10 | 1 µg Gag-DNA, 24 µg PLG | 5 | 5 |
| 2 | 10 | 10 µg Gag-DNA, 240 µg PLG | 5 | 5 |
| 3 | 10 | 10 µg Gag-DNA | 5 | 5 |

[a]Administered by IM injection on Days 0 and 28;
[b]Four weeks post-last dose;
[c]Eight weeks post-last dose Results of the PCR analysis of injection sites are presented in Table 18. Results showed that the DNA-PLG formulations were comparable to the naked-DNA control with regard to persistence. Although the Gag-DNA was still detectable at the injection site 4 and 8 weeks post-last dose, the amount remaining was insignificant (approximately $10^{-7}$% of the amount of DNA injected).

TABLE 18

PCR Analysis of Injection Sites

| Group and Treatment | Time | Mean DNA copy number[c] | Standard Deviation | % from Time 0 |
|---|---|---|---|---|
| 1 | 0 | $1.6 \times 10^{11}$ | 0 | 100 |
| 1 µg Gag-DNA, | Main Necropsy[a] | 470.6 | 378.9 | $2.9 \times 10^{-7}$ |
| 24 µg PLG | Recovery Necropsy[b] | 178.4 | 74.5 | $1.1 \times 10^{-7}$ |
| 2 | 0 | $1.6 \times 10^{12}$ | 0 | 100 |
| 10 µg Gag-DNA, | Main Necropsy[a] | 1061.4 | 432.7 | $6.6 \times 10^{-8}$ |
| 240 µg PLG | Recovery Necropsy[b] | 209 | 108.0 | $1.3 \times 10^{-8}$ |
| 3 | 0 | $1.6 \times 10^{12}$ | 0 | 100 |
| 10 µg Gag-DNA | Main Necropsy[a] | 473 | 108.7 | $3.0 \times 10^{-8}$ |
| | Recovery Necropsy[b] | 66.3 | 22.9 | $4.1 \times 10^{-8}$ |

[a]Four weeks post-last dose
[b]Eight weeks post-last dose
[c]The mean DNA copy number at time 0 was estimated based on the number of copies/µg of DNA injected.

Conclusions

Under the conditions of these studies, single and/or multiple administrations of the HIV vaccine formulation was well tolerated in animal models (New Zealand White rabbits and BALB/c mice) and, in addition, the formulations elicited potent immune responses. In the multiple-dose rabbit study, the HIV vaccine formulation produced no treatment-related adverse effects on clinical observations, body weights and temperatures, food consumption, and clinical pathology (hematology, coagulation, and clinical chemistry). Dermal scoring of injection sites revealed occasional instances of very slight to slight erythema or edema, which appeared to be reversible. These findings at the injection site are consistent with those observed in a single-dose local tolerance rabbit study. In the latter, histopathological evaluation revealed treatment-related minimal to mild inflammation at the injection site, which partially or fully resolved by the end of the recovery period. In further studies, PCR analysis of the injection sites demonstrated that the Env-DNA PLG did not integrate into the host genomic DNA and that the Gag-DNA PLG did not persist at the injection sites after 4 or 8 weeks.

In the multiple-dose rabbit study, animals received the planned clinical dose (1 mL HIV DNA vaccine, 0.5 mL HIV Protein vaccine/dose) by the clinical route of administration (IM). However, rabbits received four doses each of the HIV DNA vaccine and the HIV Protein vaccine, exceeding the intended clinical regimen (three doses each) by one dose. Further, on a body weight basis, the dose in rabbits (approximately 2.5 Kg) was approximately 24 times higher than the same dose in humans (approximately 60 Kg). Therefore, administration of the clinical dose and regimen to normal human subjects is expected to be well tolerated.

In addition, the vaccine formulations were shown to be immunogenic as high titers of antibodies Gag and Env were observed.

Example 5

Enhanced Potency of Plasmid DNA/PLG Microparticle HIV Vaccines in Rhesus Macaques Using a Prime-Boost Regimen with Recombinant Proteins The following study was conducted to determine the effect of PLG-mediated delivery on immunogenicity.

A. Preparation of Vectors, Protein, PLG

HIV vaccines as described herein were evaluated in rhesus macaques as follows. Plasmids pCMVKm2.GagMod.SF2 and pCMVKm2.o-gp140.5F162 were prepared essentially as described in U.S. Pat. No. 6,602,705. Sindbis constructs were prepared by excising the gag and env inserts from pCMVKm2 constructs and ligating them into pSINCP (a modified version of pSIN1.5, as describe essentially in Hariharan et al. (1998) J Virol 72(2):950-8).

Recombinant Env protein o-gp140SF162ΔV2 was produced in CHO cells and purified essentially as described in Srivastava et al. (2003) J Virol. 77(20):11244-11259.

Cationic PLG microparticles were prepared as follows. The microparticles were prepared using an IKA homogenizer at high speed to emulsify 10 ml of a 5% w/v polymer solution in methylene chloride with 1 mL of PBS. The primary emulsion was then added to 50 ml of distilled water containing CTAB (0.5% w/v). This resulted in the formation of a water-in-oil-in-water emulsion that was stirred at 6000 rpm for 12 hours at room temperature, allowing the methylene chloride to evaporate. The resulting microparticles were washed four times in distilled water by centrifugation at 10,000 g and freeze dried. The DNA was adsorbed onto PLG-CTAB microparticles by incubating 1 mg of DNA in 1 ml of 1×TE buffer with 100 mg of microparticles overnight at 4° C. with gentle rocking. The microparticles were then pelleted by centrifugation at 10,000 rpm for 10 minutes, washed with 1×TE buffer, re-centrifuged, and suspended in 5 ml of deionized water and freeze dried. The size distribution of the microparticles was determined using a particle size analyzer (Master sizer, Malvern Instruments, UK).

DNA constructs were adsorbed onto PLG particles are described above. Similarly, HIV p55 gag protein was adsorbed onto anionic PLG microparticles as follows. Microparticles were prepared by homogenizing 10 ml of 6% w/v polymer solution in methylene chloride with 40 ml of distilled water containing SDS (1% w/v) at high speed using a 10 mm probe. This resulted in an oil-in-water emulsion, which was stirred at 1000 rpm for 12 hours at room temperature, and the methylene chloride was allowed to evaporate. The resulting microparticles were filtered through 38 µm mesh, washed 3 times in distilled water, and freeze-dried. The size distribution of the microparticles was determined using a particles size analyzer (Master sizer, Malvern Instruments, UK).

50 mg of lyophilized SDS blank particles were incubated with 0.5 mg of p55gag protein in 10 ml 25 mM Borate buffer, pH 9, with 6M Urea. 50 mg lyophilized DSS blank microparticles were incubated with 0.5 mg of gp120 protein in 10 mL PBS. Particles were left on a lab rocker, (Aliquot mixer, Miles Laboratories) at room temperature for 5 hours. The microparticles were separated from the incubation medium by centrifugation, and the SDS pellet was washed once with Borate buffer with 6 M urea, then three times with distilled water, and lyophilized.

The loading level of protein adsorbed to microparticles was determined by dissolving 10 mg of the microparticles in 2 ml of 5% SDS-0.2 M sodium hydroxide solution at room temperature. Protein concentration was measured by BCA protein assay (Pierce Rockford, Ill.). The Zeta potential for both blank and adsorbed microparticles was measured using a Malvern Zeta analyzer (Malvern Instruments, UK).

B. Vaccination

Rhesus immunization studies were undertaken to evaluate two DNA vaccine vectors and a cationic PLG microparticle DNA delivery system in a prime-boost regimen with recombinant proteins. Groups of 5 rhesus macaques were immunized by intramuscular injection. injection on weeks 0, 4 and 14 with DNA vaccines encoding HIV SF2 Gag (0.5 mg) and HIV SF162 gp140 Env (1.0 mg) with or without adsorption to PLG microparticles. The animals were boosted with yeast-derived p55 Gag protein adsorbed onto anionic PLG microparticles (Gag/PLG) on week 29. Finally, the animals were boosted with CHO cell-derived oligomeric gp140 Env protein with a deleted V2 region administered with the oil-in-water MF59 adjuvant (Env/MF59) on weeks 38 and 75.

Immunogenicity of the vaccine compositions was assessed at various times after each immunization by quantitative and qualitative measurements of antibody (ELISA, neutralization) and T cell responses (lymphoproliferation, intracellular cytokine staining, CTL).

C. Antibody Assays

The antibody responses against Env and Gag proteins were measured by an enzyme-linked immunosorbent assay (ELISA). For both ELISA's, Nunc Maxisorp plates were coated overnight at 4° C. with 50 µl of 5 µg/ml of Env protein or Gag protein in PBS, pH 7.0. The coated wells were blocked for 1 hr at 37° C. with 150 µl of 5% goat serum (Gibco BRL, Grand Island, N.Y.) in phosphate-buffered saline (PBS). Serum samples were initially diluted 1:25 or 1:100 in the Blocking buffer followed by three-fold serial dilution. The bound antibodies were detected with horseradish peroxidase-conjugated goat anti-monkey IgG (Southern Biotechnology Associates, Inc, diluted 1:5,000 with the blocking buffer) and incubated for 1 hour at 37° C. For development, 3,3',5,5' tetramethylbenzidine (TMB) was incubated for 15 minutes according to the manufacturer's instructions, and the reaction was stopped by adding 2 N HCL. The assay plates were then read on an ELISA plate reader at an absorbance wavelength of 450 nm. A serum standard was included on each microtiter plate, and a reference value of the standard was used for the normalization of the sample ELISA titers. The titers represent the inverse of the serum dilution, giving an optical density of 0.5. Virus neutralizing antibodies were assessed against homologous HIV-1 SF162 virus, using standard techniques.

D. Purification of Rhesus PBMC and Derivation of B Lymphoblastoid Cell Lines (B-LCL)

Rhesus peripheral blood mononuclear cells (PBMC) were separated from heparinized whole blood on Ficoll-Hypaque gradients. To derive rhesus B-lymphoblastoid cell lines, PBMC were exposed to Herpesvirus papio-containing culture supernatant from the 594S cell line in the presence of 0.5 µg/ml Cyclosporin A (Sigma). Rhesus PBMC were cultured at $2-3 \times 10^6$ per well in 1.5 ml in 24-well plates for 8 days in AIM-V:RPMI 1640 (50:50) culture medium (Gibco) supplemented with 10% heat-inactivated fetal bovine serum (AR10). Antigen-specific cells were stimulated by the addition of a pool of either gag or env peptides (10.7 µg/ml total peptide). Recombinant human IL-7 (15 ng/ml, R&D Systems, Minneapolis, Minn.) was added at the initiation of culture. Human rIL2 (Proleukin, 20 IU/ml, Chiron) was added on days 1, 3, and 6.

E. $^{51}$Cr-Release Assay for CTL Activity

Autologous B-LCL were infected with recombinant vaccinia viruses (rVV) expressing gag (rVVgag-pol$_{SF2}$) or env (rVVgp160env$_{SF162}$), then labeled overnight with Na$_2$[$^{51}$Cr]O$_4$ (NEN, Boston, Mass.; 10 µCi per $2.5 \times 10^5$ B-LCL) and washed. Recombinant VV infected, $^{51}$Cr-labeled B-LCL were added (2500 per round bottom well) to duplicate wells containing 3-fold serial dilutions of cultured PBMC. Unlabeled B-LCL ($1 \times 10^5$ per well) were added to inhibit non-specific cytolysis. After 4 h, 50 µl of culture supernatant was harvested, added to Lumaplates (Packard, Meriden, Conn.) and counted with a Wallac Microbeta TriLux liquid scintillation counter (Perkin Elmer Life Sciences, Boston, Mass.). $^{51}$Cr released from lysed targets was normalized by the formula: Percent specific $^{51}$Cr release=100%×(mean experimental release−spontaneous release)/(maximum release−spontaneous release), where spontaneous release=mean counts per minute (cpm) released from target cells in the absence of PBMC and maximum release=mean cpm released from target cells in the presence of 0.1% Triton X-100. A response was scored as positive if the net specific lysis (antigen-specific minus non-specific lysis) was greater than or equal to 10% at two consecutive PBMC dilutions.

F. Lymphoproliferation Assay $2 \times 10^5$ PBMC were incubated in flat bottom microtiter wells in a volume of 0.2 ml AR10 in the absence or presence of p55 Gag protein (3 µg/ml) or a pool of Env peptides (16 µg/ml). Six replicate cultures were established. After 4 days incubation [$^3$H]-thymidine ([$^3$H]TdR, Amersham, Piscataway, N.J.) was added (1 µCi/well). Following overnight incubation, cultures were harvested onto glass microfiber filters. Cellular uptake of [$^3$H]TdR was measured with a Microbeta TriLux liquid scintillation counter (Perkin Elmer).

G. Intracellular Cytokine Staining and Flow Cytometry

Rhesus PBMC were incubated overnight at 37° C. in the absence or presence of antigen (gag peptide pool, 30 µg/ml, or env peptide pool, 30 µg/ml). Anti-CD28 (1 µg/ml, Pharmingen, San Diego, Calif.) was added as a source of costimulation and Brefeldin A (1:1000, Pharmingen) was added to prevent cytokine secretion. After overnight incubation PBMC were stained for cell surface CD4 (anti-CD4 allophycocyanin conjugate, clone SK3, Becton Dickinson, San Jose, Calif.) and CD8 (anti-CD8α PerCP conjugate, clone SK1, Becton Dickinson), permeabilized with Cytofix/Cytoperm (Pharmingen), and then stained for intracellular IFN-γ (monoclonal antibody 4S.B3, phycoerythrin conjugate, Pharmingen) and TNF-α (MAb11, FITC conjugate, Pharmingen). Stained cells were analyzed with a FACSCalibur™ flow cytometer (Becton Dickinson).

H. Comparison of DNA Vaccine Vectors

Immunogenicity of DNA vectors without PLG was evaluated. For anti-Gag antibodies, neither vector (pCMV or pSINCP) was effective when given in saline as a primary immunization regimen. However, boosting of animals primed with naked gag DNA using Gag/PLG protein antigen rapidly induced significant antibody responses. Similarly, Env/MF59 protein rapidly boosted anti-Env antibodies. At no time was there a significant difference in the antibody titers induced by pCMV or pSINCP.

Helper T cell responses were measured by both lymphoproliferation (LPA) and intracellular cytokine staining (ICS). Peripheral blood mononuclear cells (PBMC) were stimulated with recombinant p55gag protein or with a pool of synthetic env peptides. As with antibody responses, the naked pCMV and pSINCP DNA vaccines were not very effective at inducing LPA or ICS responses. However, for Gag LPA responses, pSINCP seemed to be generally more potent. Statistical significance between the pSINCP and pCMV groups was reached at weeks 20 and 27 (p=0.018, 0.023, respectively).

Similarly, pSINCP seemed to be more effective at inducing Env LPA responses. Significantly higher LPA responses between groups were observed during DNA priming at weeks 20, 24, and 27 (p=0.028, 0.022, and 0.044, respectively), as well as after the Env protein boost at week 44 (p=0.016).

To quantify T cell responses further, PBMC were stimulated overnight with antigen and then stained the PBMC with PE-conjugated anti-IFN-γ mAb and FITC-conjugated anti-TNF-α mAb (intracellular). PBMC were counterstained with APC-conjugated anti-CD4 and PerCP-conjugated anti-CD8 and analyzed by flow cytometry for cytokine-positive cells, particularly for IFN-γ/TNF-α-double positive cells, which were the most prevalent antigen-specific cells. No significant differences in frequencies of antigen-specific T cells were seen between groups of animals receiving pSINCP and pCMV.

For measurement of CTL, PBMC were cultured in the presence of a pool of gag peptides or env peptides, IL-2, and IL-7. On day 8, PBMC cultures were harvested, serially diluted, and added to microtiter wells containing $^{51}$Cr-labeled autologous B-LCL that had been infected the day before with recombinant vaccinia vectors that expressed gag (rVVgag-pol$_{SF2}$) or env (rVVgp160env$_{SF162}$). pCMV appeared more potent at inducing Gag CTL responses than pSINCP, with a greater number of responses over the course of the study. Neither DNA vaccine was effective at inducing Env CTL.

In summary, both pCMV and pSINCP naked DNA vaccines induced antibody and T cell responses against HIV Gag and Env.

I. PLG Microparticle Delivery of DNA Vaccines

Animals were also immunized as described above with DNA/PLG compositions to evaluate immunogenicity of DNA vaccines adsorbed to PLG microparticles. Adsorption of the HIV DNA vaccines onto cationic PLG microparticles was effective at enhancing immune responses, particularly for antibodies. PLG delivery markedly increased antibody titers in macaques receiving either pCMV or pSINCP. During the DNA priming phase, anti-gag titers were significantly higher in the PLG groups compared to naked DNA at every time point measured (p=0.0003 to 0.04), with peak titers ~1000-fold higher (FIG. 1). These differences were maintained after the protein boost, where pCMV/PLG and pSINCP/PLG were ~10- to 25-fold higher compared to naked DNA (p=0.02 to 0.04). Anti-Env antibody responses were also significantly higher in the PLG groups, but only at the peak response after DNA priming (2 and 6 weeks post second DNA) (P=0.003 to 0.015). Thereafter and during protein boosting, the anti-env titers were similar in all groups. For the PLG/DNA vaccine groups, peak antibody responses were observed after the second DNA immunization, whereas 3 immunizations were required for peak responses by naked DNA.

The PLG/DNA vaccines induced helper T cell responses against Gag and Env, as measured by LPA and ICS. By LPA, the magnitudes of the responses in the naked and PLG/DNA groups generally were similar, but when grouped (pCMV+pSINCP), PLG had significantly higher responses at 6 weeks for Gag and 16 weeks for Env, compared to naked DNA (p=0.05). The frequencies of cytokine production by CD4 T cells, as measured by ICS, showed enhanced responses in the Gag PLG group (pCMV+pSINCP groups combined) versus naked DNA at 2 weeks post second DNA (p<0.05). No differences were observed for the Env DNA vaccines. CD8 T cells responses were measured by ICS and $^{51}$Cr release. By ICS, the responses were generally low and no differences were seen among the groups. By $^{51}$Cr release of cultured PBMC, good CTL responses were detected against Gag, but not against Env. The total number of Gag CTL responses was 24 in the PLG groups and 18 in the naked DNA groups over the course of the study, with an apparent earlier onset of anti-Gag CTL in the pCMV/PLG group (3 of 5 animals at 2 weeks post first DNA).

In summary, PLG delivery of HIV DNA vaccines was effective at inducing antibody and cellular immune responses. Moreover, PLG significantly enhanced immunogenic responses as compared to naked DNA. Particularly strong enhancement of antibody responses was observed for both the pCMV and pSINCP DNA vaccines. For Gag, this was true during both the DNA priming and protein boosting phases of the study. Cellular immune responses also were enhanced in some cases by PLG during DNA priming, as seen by earlier onset, increased magnitude, and increased frequency of responses.

J. Protein Boosting

The animals were boosted with recombinant Gag protein adsorbed onto anionic PLG microparticles at 29 weeks, then with recombinant Env in MF59 adjuvant at 38 and 75 weeks (15, 24, and 51 weeks, respectively, after the last DNA immunization). Antibody titers were boosted markedly in all groups (FIGS. 1,2). After boosting with gag protein the anti-gag antibody titers were approximately tenfold higher in the animals primed with PLG/CTAB-DNA than those primed with naked DNA. The anti-gag titers equaled (DNA/PLG) or exceeded (DNA/saline) the peak titers achieved by DNA priming. For Env, titers in all groups were significantly boosted above peak titers after DNA priming (p=0.0002 to 0.02) (FIG. 2). The second Env protein boost restored antibody titers to levels seen after the first Env protein boost. Virus-neutralizing antibody responses were not detected in any animals after DNA vaccine priming. However, increasing titers were observed after one and two protein booster immunizations, with overall geometric mean titers of 8 and 64, respectively (p=0.00071) (FIG. 3). At both of these time points, the titers were not statistically different among the various vaccine groups.

T cell responses also appeared to be boosted after protein immunization. For Gag, mean SI increased 4- to 7-fold over baseline after protein boosting, with the number of responders increasing from 7 to 14 (out of 20). However, the magnitude of the responses was not higher than those seen at the peak after DNA priming.

Figure 4:
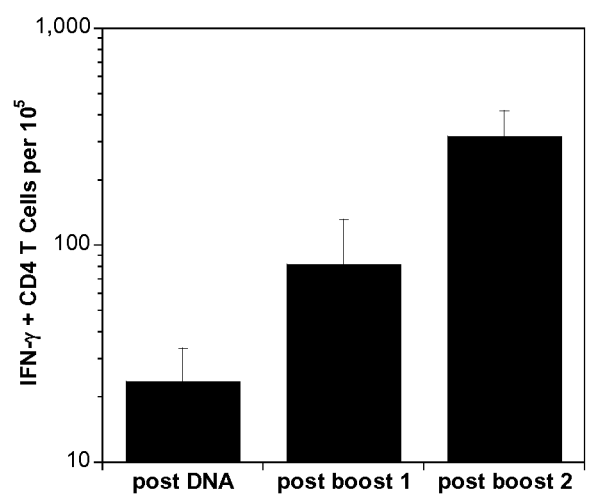
FIG. 4 is a graph depicting the effect of Env protein boosting on T cell responses primed by DNA vaccines.

After Env protein boosting, mean SI increased 11- to 25-fold over baseline and these responses were higher than those measured after DNA priming. By ICS, little or no increases were observed after Gag protein boosting, but substantial increases in the proportion of cells secreting IFN-γ and TNF-α were seen after each Env protein boosting. Furthermore, the overall magnitude of the ICS response was higher after the second compared to the first protein boost (p=0.0008) (FIG. 4), with responses approaching 4% of CD4 T cells in some animals. As expected, CTL responses were not boosted by protein immunization.

In summary, boosting DNA-primed macaques with recombinant Gag and Env proteins resulted in rapid and significant enhancement of antibody and T cell responses. In some cases, the magnitude of these responses was markedly higher than achieved after DNA priming.

Thus, DNA/PLG vaccines as described herein induce strong immune responses in rhesus macaques, with particular enhancement of antibody responses and an effect on helper and cytotoxic T cells. The effectiveness of boosting DNA/PLG-primed macaques with recombinant protein was also established, including strong Th1-type cytokine production from T cells after Env protein boosting.

Example 6

Human Studies

Based on data from previous HIV vaccine trials (with other products), the rate of serious adverse experiences in the placebo controls is approximately 3.5%. Extensive safety data on the use of other recombinant glycoprotein antigens with MF59 indicate that such vaccine antigens, when administered with MF59, are very safe and generally well tolerated. Additionally, these vaccines have elicited a strong antibody response against the particular antigens.

An exemplary protocol for human studies is shown below in Table 19. Although exemplified with regard to subtype B, it will readily apparent that the protocol can also be used as is, or with modifications, for other strains or subtypes of HIV.

TABLE 19

Human Protocol
STUDY AGENTS
A: Clade B Gag + Env DNA/PLG microparticles, dose indicated below (μg)
B: Clade B gp140 Env protein, 100 μg
P: Placebo: PBS

| Group | #/grp | DNA dose | Protein dose | 0 (0) | 1 (28) | 2 (56) | 4 (112) | 6 (168) | 9 (236) |
|---|---|---|---|---|---|---|---|---|---|
| PART ONE | | | | | | | | | |
| 1 | 10 | 250/250 | 100 μg | A | A | A | | B | B |
|   | 2 | Placebo | | P | P | P | | P | P |
| 2 | 10 | 500/500 | 100 μg | A | A | A | | B | B |
|   | 2 | Placebo | | P | P | P | | P | P |
| 3 | 10 | 1000/1000 | 100 μg | A | A | A | | B | B |
|   | 2 | Placebo | | P | P | P | | P | P |
| PART TWO | | | | | | | | | |
| 4 | 20 | 1000/1000 | 100 μg | A | A | A | | B | B |
|   | 4 | Placebo | | P | P | P | | P | P |
| 5 | 30 | 1000/1000 | 100 μg | A | A | | | A + B | B |
|   | 6 | Placebo | | P | P | | | P | P |
| 6 | 30 | 1000/1000 | 100 μg | A | A | | A + B | B | |
|   | 6 | Placebo | | P | P | | P | P | |
| 7 | 30 | 1000/1000 | 100 μg | A | A | | | B | B |
|   | 6 | Placebo | | P | P | | | P | P |
| TOTAL: | 168 | | | | | | | | |

What is claimed is:

1. A method of generating an immune response in a subject, said method comprising: (a) administering to the subject at least two polynucleotide immunogenic compositions each comprising a nucleic acid expression vector comprising at least one HIV Env-encoding polynucleotide sequence, wherein the at least two polynucleotide immunogenic compositions are administered separately; and (b) administering to the subject, at a time subsequent to the administering of step (a), at least two polypeptide immunogenic compositions each comprising an HIV ogp140, wherein the at least two polypeptide immunogenic compositions are administered separately.

2. The method of claim 1, wherein step (a) comprises two or three administrations at one month intervals; step (b) comprises two or three administrations at 1, 2 or 3 month intervals; and the time between the administrations of step (a) and step (b) is 1 to 5 months.

3. A method of generating an immune response in a subject, said method comprising: administering to the subject at least two polypeptide immunogenic compositions each comprising an HIV ogp140, wherein the at least two polypeptide immunogenic compositions are administered separately and wherein the subject has previously been administered at least two polynucleotide immunogenic compositions each comprising a nucleic acid expression vector comprising at least one HIV Env-encoding polynucleotide sequence, wherein the at least two polynucleotide immunogenic compositions were administered separately.

4. The method of claim 1, wherein the administering at least two polypeptide immunogenic composition comprises two or three administrations at 1, 2 or 3 month intervals; the subject has received two or three administrations of said at least two polynucleotide immunogenic composition at one month intervals; and the time between the administration of the last polynucleotide immunogenic composition and the first polypeptide immunogenic composition is 1 to 5 months.

5. The method of claim 1 or claim 3, wherein the administering is intramuscular or intradermal.

6. The method of claim 1 or claim 3, wherein the polypeptide immunogenic composition further comprises a pharmaceutically acceptable excipient.

7. The method of claim 1 or claim 3, wherein the ogp140 is at a concentration between about 0.1 and 10 mg/mL.

8. The method of claim 1 or claim 3, wherein the ogp140 per dose is approximately 100 μg/dose.

9. The method of claim 1 or claim 3, wherein the polypeptide immunogenic composition further comprises an adjuvant.

10. The method of claim 9, wherein the adjuvant is an oil-in-water emulsion or CpG.

11. The method of claim 10, wherein the adjuvant is an oil-in-water emulsion and the oil-in-water emulsion comprises squalene.

12. The method of claim 11, wherein the oil-in-water emulsion is MF59™.

13. The method of claim 11, wherein the oil-in-water emulsion comprises 39 mg/ml squalene, 4.7 mg/ml polysorbate 80, 4.7 mg/ml sorbitan trioleate, 2.68 mg/ml sodium citrate dihydrate, 0.17 mg/ml citric acid monohydrate.

14. The method of claim 1 or claim 3, wherein the polynucleotide immunogenic composition further comprises polymer microparticles and the nucleic acid expression vector is adsorbed to the polymer microparticles.

15. The method of claim 14, wherein the polymer Microparticles are poly(lactides) or poly(lactide-co-glycolides) (PLG).

16. The method of claim 1 or claim 3, wherein the HIV ogp140 is from HIV Clade C.

* * * * *